(12) United States Patent
Manohara et al.

(10) Patent No.: US 9,549,667 B2
(45) Date of Patent: Jan. 24, 2017

(54) ENDOSCOPE AND SYSTEM AND METHOD OF OPERATION THEREOF

(71) Applicants: Harish M. Manohara, Arcadia, CA (US); Anna Liao, Montrose, CA (US); Youngsam Bae, Los Angeles, CA (US); Hrayr Karnig Shahinian, Beverly Hills, CA (US)

(72) Inventors: Harish M. Manohara, Arcadia, CA (US); Anna Liao, Montrose, CA (US); Youngsam Bae, Los Angeles, CA (US); Hrayr Karnig Shahinian, Beverly Hills, CA (US)

(*) Notice: Subject to any disclaimer, the term of this patent is extended or adjusted under 35 U.S.C. 154(b) by 474 days.

(21) Appl. No.: 13/692,573

(22) Filed: Dec. 3, 2012

(65) Prior Publication Data
US 2013/0096381 A1 Apr. 18, 2013

Related U.S. Application Data

(62) Division of application No. 12/338,984, filed on Dec. 18, 2008, now Pat. No. 8,232,182.

(51) Int. Cl.
*A61B 1/04* (2006.01)
*A61B 1/00* (2006.01)
(Continued)

(52) U.S. Cl.
CPC ............ *A61B 1/045* (2013.01); *A61B 1/00039* (2013.01); *A61B 1/00045* (2013.01);
(Continued)

(58) Field of Classification Search
CPC ............ A61B 1/00174; A61B 1/00177; A61B 1/00179; A61B 1/00181; A61B 1/00183; A61B 1/0125; A61B 1/00045; A61B 1/00048; A61B 1/0005
(Continued)

(56) References Cited

U.S. PATENT DOCUMENTS

| | | |
|---|---|---|
| 1,960,011 A | 5/1934 | Ives |
| 2,255,631 A | 9/1941 | Shulman |

(Continued)

FOREIGN PATENT DOCUMENTS

| | | |
|---|---|---|
| EP | 0469966 B1 | 2/1992 |
| EP | 1371321 A1 | 12/2003 |

(Continued)

OTHER PUBLICATIONS

Y.S. Heo, "Illumination and Camera Invariant Stereo Matching," Computer Vision and Pattern Recognition, 2008. CVPR 2008. IEEE Conference, vol., No., pp. 1-8, Jun. 23-28, 2008.

(Continued)

*Primary Examiner* — Timothy J Neal

(57) ABSTRACT

An endoscope including a rigid section having opposed first and second ends and an opening situated between the first and second ends, the rigid section defining a longitudinal axis; a handle portion coupled to a first end of the rigid section and having first and second scissor-type handles suitable for grasping by a user; and a base part situated at the second end of the rigid section and coupled to the first handle of the scissor-type handles such that displacement of the first handle causes a rotation of the base part.

18 Claims, 23 Drawing Sheets

(51) Int. Cl.
*A61B 1/045* (2006.01)
*A61B 1/05* (2006.01)
*A61B 1/06* (2006.01)
*A61B 1/313* (2006.01)

(52) U.S. Cl.
CPC ............ *A61B 1/00183* (2013.01); *A61B 1/05* (2013.01); *A61B 1/051* (2013.01); *A61B 1/0676* (2013.01); *A61B 1/0684* (2013.01); *A61B 1/3132* (2013.01)

(58) Field of Classification Search
USPC .................. 600/109, 11, 118, 139, 141, 142
See application file for complete search history.

(56) References Cited

U.S. PATENT DOCUMENTS

| | | |
|---|---|---|
| 3,870,037 A | 3/1975 | Cadariu et al. |
| 4,651,201 A | 3/1987 | Schoolman |
| 4,759,348 A | 7/1988 | Cawood |
| 4,761,066 A | 8/1988 | Carter |
| 4,873,572 A | 10/1989 | Miyazaki et al. |
| 4,877,307 A | 10/1989 | Kalmanash |
| 4,951,676 A | 8/1990 | Collet-Billon |
| 5,050,226 A | 9/1991 | Collet-Billon |
| 5,105,269 A | 4/1992 | Nakamura et al. |
| 5,192,969 A | 3/1993 | Igarashi et al. |
| 5,222,477 A | 6/1993 | Lia |
| 5,305,098 A | 4/1994 | Matsunaka et al. |
| 5,395,030 A | 3/1995 | Kuramoto et al. |
| 5,436,655 A | 7/1995 | Hiyama et al. |
| 5,459,605 A | 10/1995 | Kempf |
| 5,471,237 A | 11/1995 | Shipp |
| 5,494,483 A | 2/1996 | Adair |
| 5,536,234 A | 7/1996 | Newman |
| 5,540,229 A | 7/1996 | Collet-Billon et al. |
| 5,547,455 A | 8/1996 | McKenna et al. |
| 5,603,687 A | 2/1997 | Hori et al. |
| 5,605,532 A | 2/1997 | Schermerhorn |
| 5,662,584 A | 9/1997 | Hori et al. |
| 5,667,473 A | 9/1997 | Finn et al. |
| 5,697,891 A | 12/1997 | Hori |
| 5,743,847 A | 4/1998 | Nakamura et al. |
| 5,751,341 A | 5/1998 | Chaleki et al. |
| 5,782,752 A | 7/1998 | Lichtman et al. |
| 5,782,859 A * | 7/1998 | Nicholas ............ A61B 17/0218 600/204 |
| 5,810,716 A | 9/1998 | Mukherjee et al. |
| 5,817,014 A | 10/1998 | Hori et al. |
| 5,823,940 A | 10/1998 | Newman |
| 5,827,323 A * | 10/1998 | Klieman et al. ............ 606/205 |
| 5,828,487 A | 10/1998 | Greening et al. |
| 5,835,194 A | 11/1998 | Morton |
| 5,841,887 A | 11/1998 | Kuwayama et al. |
| 5,855,549 A | 1/1999 | Newman |
| 5,895,350 A | 4/1999 | Hori |
| 5,928,137 A | 7/1999 | Green |
| 5,935,057 A | 8/1999 | Lichtman et al. |
| 5,941,817 A | 8/1999 | Crawford |
| 5,941,818 A | 8/1999 | Hori et al. |
| 5,944,654 A | 8/1999 | Crawford |
| D415,146 S | 10/1999 | Hori |
| 5,964,696 A | 10/1999 | Mihalca et al. |
| 5,984,939 A | 11/1999 | Yoon |
| 5,989,182 A | 11/1999 | Hori et al. |
| 6,046,727 A | 4/2000 | Rosenberg et al. |
| 6,050,939 A | 4/2000 | Pak Wai |
| 6,066,090 A | 5/2000 | Yoon |
| 6,086,528 A | 7/2000 | Adair |
| 6,159,146 A | 12/2000 | El Gazayerli |
| 6,191,809 B1 | 2/2001 | Hori et al. |
| 6,211,848 B1 | 4/2001 | Plesniak et al. |
| 6,223,100 B1 | 4/2001 | Green |
| 6,277,064 B1 | 8/2001 | Yoon |
| RE37,356 E | 9/2001 | Hori et al. |
| 6,290,649 B1 | 9/2001 | Miller et al. |
| 6,292,221 B1 | 9/2001 | Lichtman |
| 6,306,082 B1 | 10/2001 | Takahashi et al. |
| 6,313,883 B1 | 11/2001 | Thaler |
| 6,419,626 B1 | 7/2002 | Yoon |
| 6,445,814 B2 | 9/2002 | Lijima et al. |
| 6,450,948 B1 | 9/2002 | Matsuura et al. |
| 6,450,950 B2 * | 9/2002 | Irion ............................ 600/170 |
| 6,517,479 B1 | 2/2003 | Sekiya et al. |
| 6,593,957 B1 | 7/2003 | Christie |
| 6,624,935 B2 | 9/2003 | Weissman et al. |
| 6,647,792 B2 | 11/2003 | Ogawa |
| 6,731,988 B1 | 5/2004 | Green |
| 6,817,973 B2 | 11/2004 | Merril et al. |
| 6,832,984 B2 | 12/2004 | Stelzer et al. |
| 6,916,286 B2 * | 7/2005 | Kazakevich .................. 600/173 |
| 6,976,956 B2 | 12/2005 | Takahashi et al. |
| 6,980,676 B2 | 12/2005 | Pineau |
| 6,991,602 B2 | 1/2006 | Nakazawa et al. |
| 6,997,871 B2 | 2/2006 | Sonnenschein et al. |
| 7,043,062 B2 | 5/2006 | Gerard et al. |
| RE39,342 E | 10/2006 | Starks et al. |
| 7,153,259 B2 | 12/2006 | Matsuzawa et al. |
| 7,154,527 B1 | 12/2006 | Goldstein et al. |
| 7,241,262 B2 | 7/2007 | Adler et al. |
| 7,553,277 B2 | 6/2009 | Hoefig et al. |
| 7,601,119 B2 | 10/2009 | Shahinian |
| 7,621,869 B2 | 11/2009 | Ratnakar |
| 2002/0030678 A1 | 3/2002 | Ostermann |
| 2002/0049367 A1 | 4/2002 | Irion et al. |
| 2002/0154215 A1 | 10/2002 | Schechterman et al. |
| 2003/0053744 A1 | 3/2003 | Makio |
| 2003/0125608 A1 | 7/2003 | Igarashi |
| 2003/0174208 A1 | 9/2003 | Glukhovsky et al. |
| 2003/0233024 A1 | 12/2003 | Ando |
| 2004/0019255 A1 | 1/2004 | Sakiyama |
| 2004/0070667 A1 | 4/2004 | Ando |
| 2004/0249367 A1 | 12/2004 | Saadat et al. |
| 2005/0065657 A1 | 3/2005 | Green |
| 2005/0065658 A1 | 3/2005 | Green |
| 2005/0119530 A1* | 6/2005 | Douglas et al. ............. 600/212 |
| 2005/0228230 A1 | 10/2005 | Schara et al. |
| 2005/0234296 A1 | 10/2005 | Saadat et al. |
| 2005/0234297 A1 | 10/2005 | Devierre et al. |
| 2005/0261548 A1 | 11/2005 | Machiya et al. |
| 2005/0278711 A1 | 12/2005 | Silva et al. |
| 2006/0015008 A1 | 1/2006 | Kennedy |
| 2006/0111614 A1 | 5/2006 | Saadat et al. |
| 2006/0224040 A1 | 10/2006 | Khait et al. |
| 2006/0247495 A1 | 11/2006 | Bacher et al. |
| 2007/0055103 A1* | 3/2007 | Hoefig et al. .................. 600/173 |
| 2007/0112256 A1 | 5/2007 | Terakawa |
| 2007/0173689 A1 | 7/2007 | Ozaki et al. |
| 2007/0225550 A1* | 9/2007 | Gattani .................. A61B 19/52 600/101 |
| 2007/0249932 A1 | 10/2007 | Shahinian |
| 2007/0255100 A1 | 11/2007 | Barlow et al. |
| 2008/0243142 A1* | 10/2008 | Gildenberg ............ A61B 19/52 606/130 |
| 2008/0281154 A1 | 11/2008 | Gono et al. |
| 2008/0284982 A1 | 11/2008 | Richards et al. |
| 2009/0137893 A1 | 5/2009 | Seibel et al. |
| 2009/0187072 A1 | 7/2009 | Manohara et al. |
| 2010/0006549 A1 | 1/2010 | Pahk et al. |
| 2011/0115882 A1 | 5/2011 | Shahinian et al. |

FOREIGN PATENT DOCUMENTS

| | | |
|---|---|---|
| EP | 1854420 A1 | 11/2007 |
| EP | 1880657 A1 | 1/2008 |
| EP | 1989990 A1 | 11/2008 |
| JP | 04-021105 | 1/1992 |
| JP | 06-202004 | 7/1994 |
| JP | 06-237892 | 8/1994 |
| JP | 10-010468 | 1/1998 |
| JP | 2000-052289 | 2/2000 |
| WO | 93/13916 A1 | 7/1993 |
| WO | 96/35975 A1 | 11/1996 |
| WO | 99/57900 A1 | 11/1999 |

(56) References Cited

FOREIGN PATENT DOCUMENTS

| WO | 00/50927 A2 | 8/2000 |
|---|---|---|
| WO | 00/61009 A1 | 10/2000 |
| WO | 0237142 A2 | 5/2002 |
| WO | 03098913 A2 | 11/2003 |
| WO | 2005/030328 A2 | 4/2005 |
| WO | 2005/031433 A1 | 4/2005 |
| WO | 2005/120327 A2 | 12/2005 |
| WO | 2008/033356 A2 | 3/2008 |

OTHER PUBLICATIONS

J.L. Garb, "Using GIS for spatial analysis of rectal lesions in the human body," International Journal of Health Geographics, 2007, 6:11, Published online Mar. 15, 2007. doi: 10.1186/1476-072X-6-11. PMCID: PMC1839078 BioMed Central Ltd.

J.P. Rice, "A hyperspectral image projector for hyperspectral imagers," SPIE vol. 6565 65650C, (2007).

J.P. Rice, "Hyperspectral image projectors for radiometric applications," BIPM and IOP Publishing Ltd, Metrologia 43 (2006) S61-S65.

J.P. Rice, "Development of hyperspectral image projectors," SPIE vol. 6297, 629701, (2006).

J.M. Medina, "Binocular interactions in random chromatic changes at isoluminance," Opt. Soc. Am., 2006, vol. 23, No. 2, pp. 239-246.

A. Szold, "Seeing is believing—Visualization systems in endoscopic surgery (video, HDTV, stereoscopy, and beyond)," Surgical Endoscopy, 19:55, pp. 730-733, Springer, 2005.

U. D. A Mueller-Richter,"Possibilities and limitations of current stereo-endoscopy," Journal of Surgical Endoscopy, Springer, New York, ISSN 0930-2794 (Print) 1432-2218 (Online) Issue vol. 18, No. 6, Jun. 2004, 18: pp. 942-947.

M.A. Weissman, "Stereo parallax and Disnparity in Single-Lens Stereoscopy," Stereoscopic Displays and Virtual Reality Systems VII, SPIE 3987, pp. 312-320, Apr. 2000.

G.A. Lester, "Ferroelectric liquid crystal device for a single camera stereoscopic endoscope system," Electronics Letters, 1997, vol. 33, No. 10, pp. 857-858.

G.L. Zimmerman, "Perception at Equiluminance: An Adaptive Model of Motion Metamers," Circuits and Systems, 1994., Proceedings of the 37th Midwest Symposium on , vol. 1, No., pp. 577-580 vol. 1, Aug. 3-5, 1994.

Y. Takemura, "Stereoscopic Video Movie Camera Using 300k Pixel IT-CCD Sensors," IEEE Transactions on Consumer Electronics, Feb. 1991, vol. 37, No. 1, pp. 39-44.

E. Badique, "Use of color image correlation in the retrieval of gastric surface topography by endoscopic stereopair matching," Applied Optics, 1988, vol. 27, No. 5, pp. 941-948.

N. Ohyama, "Compensation of motion blur in CCD color endoscope images," Opt. Soc. Am., 2006, Applied Optics, 1987, vol. 26, No. 5, pp. 909-912.

P. Breedveld and M. Wentink, "Eye-hand coordination in laparoscopy—an overview of experiments and supporting aids," Min Invas Ther & Allied Technol 2001: 155-162, 10(3).

Keijirou Itakura, et al., "A 1-mm 50 k-Pixel IT CCD Image Sensor for Miniature Camera System," IEEE Transactions on Electron Devices, Jan. 2000, 65-70, vol. 47, No. 1.

Jacques Duparré, et al., "Thin compound-eye camera," Applied Optics, May 20, 2005, pp. 2949-2956, vol. 44, No. 15.

Jun Tanida, et al., "Color imaging with an integrated compound imaging system," Optics Express, Sep. 8, 2003, 2019-2117, vol. 11, No. 18.

Jun Tanida, et al., "Thin observation module by bound optics (TOMBO): concept and experimental verification," Applied Optics, Apr. 10, 2001, 1806-1813, vol. 40, No. 11.

Ikeda, M., Sagawa, K., "Binocular color fusion limit," J. of the Optical Society of America, 69(2), 316-321, (Feb. 1979).

Dudley, D., Duncan, W. M., Slaughter, J., "Emerging digital miromirror device (DMD) applications," Proceedings of SPIE 4985, 14-25 (2003).

Hovis, J. K., "Review of Dichoptic Color Mixing," Optometry and Vision Science, 66(3), 181-190 (1998).

Lambooij, M., Ijsselsteijn, W., "Visual discomfort and visual fatigue of stereoscopic display: A review," J. of Imaging science and technology, 53(3), 030201 (2009).

DooHyun Lee and InSo Kweon, "A Novel Stereo Camera System by a Biprism," IEEE Transactions on Robotics and Automation, 16(5), 528-541, (Oct. 2000).

Mikko Kyto, Mikko Nuutinen, Pirkko Oittinen, "Method for measuring stereo camera depth accuracy based on stereoscopic vision," OAalto University School of Science and Technology, Department of Media Technology, Otaniementie 17, Espoo, Finland.

Qin, D., Takamatsu, M., Nakashima, Y., Qin, X., "Change of wavelength difference limit for binocular color fusion with wavelength and brightness of stimuli," J. of Light and Visual Environment, 30(1), 43-45 (2006).

Jung, Y. J., Sohn, H., Lee, S., Ro, Y. M., and Park, H. W., "Quantitative measurement of binocular color fusion limit for non-spectral colors.," Optics express, 19(8), 7325-7338 (2011).

Planar Systems Inc., "SD1710 Pruduct User's Guide," 1-12 (2005).

CRI Varispec, "Liquid Crystal Tuneable Filters," 1-12 (2005).

Avi Yaron, Mark Shechterman and Nadav Horesh, "Blur spot limitations in distal endoscope sensors," Proc. SPIE 6055, Stereoscopic Displays and Virtual Reality Systems XIII, 605509 (Jan. 27, 2006).

Researchers Work on Snake-Like 'Rescue Robots', downloaded on Apr. 20, 2006 from http://www.foxnew5.com/printer_friendly_story/O,3566, 192430,OO.htm.

NASA Infrared Camera Helps Surgeons Map Brain Turners, Jul. 15, 2004,downloaded on Apr. 24, 2006 from http://www.jpl.nasa.gov/news/news.cfm?release=20D4-183.

Fung et al., "A Case Study of 3D Stereoscopic VS. 20 Monoscopic Tele-Reality In . . . " IEEE/RSJ International Conference on Intelligent Robots and Systems, 2005, pp. 181-186.

Nain et al., "Three-Dimensional Nanoscale Manipulation and Manufacturing Using Proximal Probes: Controlled Pulling of Polymer . . . " IEEE Int Conf Rob Autom vol. 1,2004, pp. 434-439.

Lytle et al., Adapting a Teleoperated Device for Autonomous Control Using Three-Dimensional Positioning sensors: . . . Automation in Construction, vol. 13, 2004, pp. 101-118.

Mezouar et al., Robustness of Central Catadioptric Image-based Visual . . . • IEEE RSJ Int. Conf. Intell. Robots and Syst. IROS, vol. 2, Sep. 28-Oct. 2, 2004, Sendai, JP, pp. 1389-1394.

Murakami et al., "Automatic Insertion Work. Based on Visual Measurement and Contact Force Estimation" Proc IEEE Int Conf Rob Autom, vol. 4, May 2002, pp. 4167-4172.

Trivedi et al., "A Vision System for Robotic Inspection and Manipulation", DE90 005412, Univ of Tennessee, Revised Mar. 1989. pp. 1-12.

Nguyen et al., "30 Model Control of Image Processing" In JPL, California Inst. of Tech., Proceedings of the NASA Conference on Space Telerobotics, vol. 3, pp. 213-222 May 2000.

Stiel et af. Digital Flashing Tomosynthesis: A Promising Technique for Angiocardiographic ScreeningD IEEE Transactions on Medical Imaging, Jun. 1993, No. 2, NY, pp. 314-321.

Fritz, Eric., "High Speed Generation of Illumination Spectra for a Stereoscopic Endoscope", http://hdl.handle.net/2014/42272, NASA Undergraduate Student Research Program (USRP), Pasadena, California, Aug. 9, 2011, pp. 1-8, Retrieved from Internet: URL: http://trs-new.jpl.nasa.gov/dspace/bitstream/2014/42272/1/11-3811.pdf.

Ream, Allen, "Project report: reducing color rivalry in imagery for conjugated multiple bandpass filter based stereo endoscopy", http://hdl.handle.net/2014/42276, NASA Undergraduate Student Research Program (USRP), Pasadena, California, Aug. 2011, pp. 1-9, Retrieved from Internet: URL: http://trs-new.jpl.nasa.gov/dspace/bitstream/2014/42276/1/11-3803.pdf.

J.P. Rice et al., "Hyperspectral image compressive projection algorithm," SPIE vol. 7334 pp. 733414-1, , XP055046293, ISSN: 0277-786X, DOI: 10.1117/12.818844, (Apr. 27, 2009).

Sam Bae et al, "Toward a 3D endoscope minimally invasive surgery", SPIE Newsroom, Sep. 21, 2011, pp. 1-3, XP055046098, DOI: 10.1117/2.1201109.003810.

(56) References Cited

OTHER PUBLICATIONS

NASA's Jet Propulsion Laboratory et al: "Stereo Imaging Miniature Endoscope", Internet Citation, Jun. 30, 2011 (Jun. 30, 2011), pp. 6-7, XP002687431, Retrieved from the Internet: URL:http://ntrs.nasa.gov/archive/nasa/casi.ntrs.nasa.gov/20110012587_2011013131.pdf [retrieved on Dec. 3, 2012].

Ronald Korniski et al: "3D imaging with a single-aperture 3-mm objective lens: concept, fabrication, and test", Proceedings of SPIE, vol. 8144, Sep. 14, 2011 (Sep. 14, 2011), p. 812904, XP055046246, ISSN: 0277-786X, DOI: 10.1117/12.894110.

\* cited by examiner

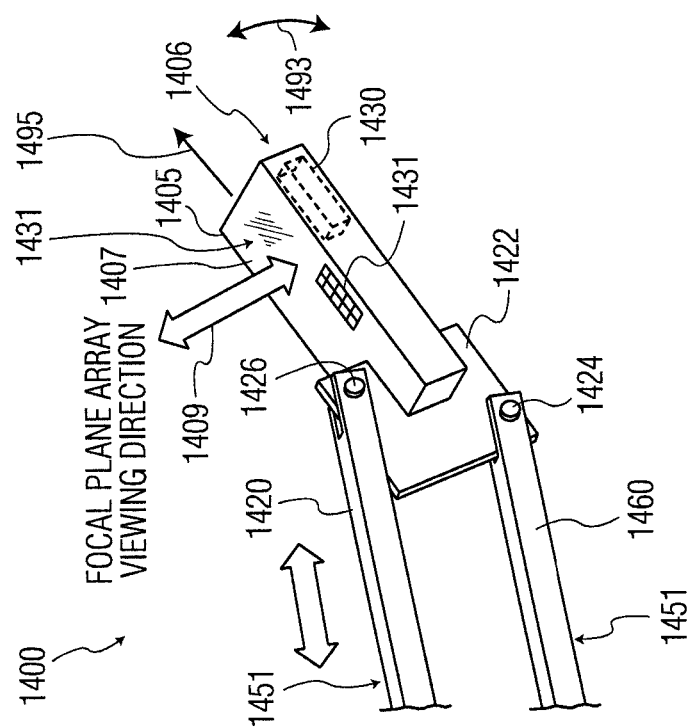
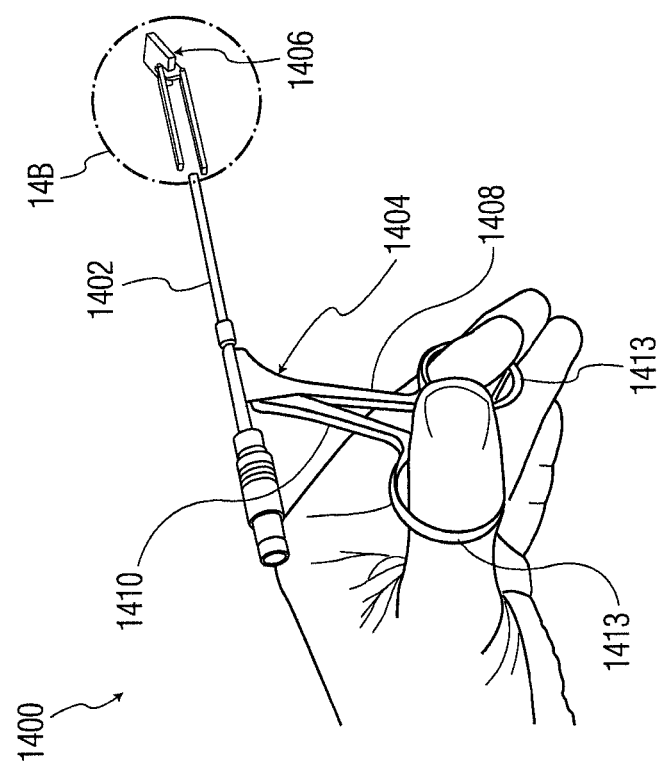
FIG. 14B
FIG. 14A

ENDOSCOPE AND SYSTEM AND METHOD OF OPERATION THEREOF

This application is a divisional of prior U.S. patent application Ser. No. 12/338,984, filed Dec. 18, 2008.

This application claims the benefits of U.S. Provisional Patent Application Ser. No. 61/008,033 filed Dec. 18, 2007, and U.S. Provisional Patent Application Ser. No. 61/127,496 filed May 14, 2008, which are both incorporated herein by reference in their entireties.

The invention described herein was made in the performance of work under a NASA contract, and is subject to the provisions of Public Law 96-517 (35 USC 202) in which the Contractor has elected to retain title.

The present system relates generally to medical imaging systems and, more particularly, to an endoscopic viewing system having an adjustable viewing angle which can provide a rear view, and a method of operation thereof.

Minimally invasive procedures can include surgical and other procedures, which are typically less invasive than traditional open procedures such as, for example, open surgery. A typical minimally invasive surgical (MIS) procedure usually involves the manipulation of one or more endoscopic devices that can be inserted through an opening or incision and an endoscope or the like to observe a surgical area (or field).

During minimally invasive endoscopic (e.g., laparoscopic) surgical procedures, surgeons typically utilize endoscopes to view a surgical field and thereby acquire a clear view of anatomical structures in the surgical field. As minimally invasive surgery is typically performed through a small opening or incision, surgeons cannot view the surgical field directly but must rely instead upon an endoscope to provide an image of a surgical field. As the small opening or incision through which the endoscope passes is typically about the size of a dime, the range of operation of the endoscope within a surgical field is typically limited. Further, as most endoscopes typically provide a forward line-of-sight image, a surgeon may have to rely upon a compromised view of a surgical field during a minimally invasive surgical procedure.

With respect to endoscopes, these devices typically fall into two types: a fixed (or rigid) type and a flexible type. The fixed type typically includes a fixed body portion and the flexible type includes a flexible body portion.

With regard to the typical fixed-type endoscope, the viewing portion (which is used to obtain real-time images) on this endoscope only provides a forward view as opposed to a rearview (e.g., a view towards a handle side of the endoscope). Thus, the typical fixed-type endoscope can only provide a forward view of an operating field. Accordingly, in order to obtain a rear view of a surgical field it may be necessary to insert another endoscope into another incision. However, making another incision may not always be possible and may also have a detrimental effect on a patient and on a surgical procedure being performed.

Further, with regard to a flexible-type endoscope, although this endoscope can be manipulated to move a viewing portion, it is difficult to determine where the viewing portion is located and a direction in which the viewing portion is pointing. Accordingly, it is difficult to determine a viewing orientation of a flexible-type endoscope and, thus, difficult to determine a spatial orientation with respect to a surgical field. Accordingly, flexible-type endoscopes may not be suitable for viewing a surgical field during surgery.

Accordingly, there is a need for an endoscope that can provide a rear view of a surgical field.

One object of the present systems, methods, apparatuses, and devices (hereinafter system unless context indicates otherwise) is to overcome the disadvantages of conventional systems and devices. According to one illustrative embodiment, a medical imaging system may include an endoscope including: a rigid section having opposed first and second ends and an opening situated between the first and second ends, the rigid section defining a longitudinal axis; a handle portion coupled to a first end of the rigid section and having first and second scissor-type handles suitable for grasping by a user; and a base part having an image capturing device, the base part situated at the second end of the rigid section and coupled to the first handle of the scissor-type handles such that a displacement of the one of the scissor-type handles relative to the other of the scissor-type handles causes a change in a viewing direction of image capturing device.

The base part may further include a reflective optical element. Further, the endoscope may include a biasing member which biases at least one of the first and second scissor-type handles relative to the other of the first and second scissor-type handles. The endoscope may further include a rigid shaft located in the opening and operatively coupling the first handle of the scissor-type handles and the base part. The shaft may telescope within the opening and/or maintain a fixed shape when the shaft telescopes within the opening. Further, when the first handle may be located in a first region of travel, the viewing direction is may be along the longitudinal axis and in a direction which may be towards the first end of rigid section. The endoscope may also include a brake to lock the base part in a fixed position. The image capturing device may include at least one of a charge coupled device (CCD) and complementary metal oxide semiconductor (CMOS) device. The endoscope may also include one or more reflective optical elements coupled to the base so as to reflect an image. The image capturing device may also include an image capturing device which may be suitable for providing two and/or three dimensional image information. Thus, for example, a stereoscopic imaging system may be provided. Further, the image capturing device may include two or more image capturing devices which may be situated apart from each other so as to provide suitable three dimensional images.

According to another aspect of the present system, there is disclosed a method for operating an endoscope including a rigid section defining a longitudinal axis and having first and second scissor-type handles suitable for grasping by a user coupled thereto, the method may include the acts of: capturing images from an image capturing device hingedly coupled to the rigid section, the image capturing device capturing the images in a first field of view; and changing the position of the camera relative to the rigid section so as to change the viewing direction of the camera to a further viewing direction by displacing the first scissor-type handle relative to the second scissor-type handle.

The method may also include an act of biasing the first scissor-type handle relative to the second scissor-type handle using a biasing member. The further viewing direction of the image capturing device may correspond with a rear-viewing direction.

The method may further include the act of operatively coupling the first scissor-type and the camera via a rigid shaft located in the opening of the rigid section.

The method may also include the act of locking the base part in a fixed position relative to the rigid section using a brake, and/or transmitting the captured images using a transmitter.

The method may further include the act of adjusting a position of a reflective optical element so as to adjust a rearward image viewing direction of the image capturing device.

According to a further aspect of the present system, there is disclosed an endoscopic imaging system including: an endoscope including: a rigid section having opposed first and second ends and an opening situated between the first and second ends, the rigid section defining a longitudinal axis, first and second scissor-type handles suitable for grasping by a user and located adjacent to a first end of the rigid section; and an image capturing device camera situated at a second end of the rigid section and coupled to the first scissor-type handle such that displacement of the first handle causes a change in a viewing direction of the image capturing device.

The endoscopic imaging system may also include a transmitter which transmits images captured by the image capturing device. Further, the endoscopic imaging system may include a receiver which receives the images captured by the image capturing device.

The endoscopic imaging system may also include a display which displays the images received by the receiver. This display may include a two or a three dimensional display. The endoscopic imaging system may further include one or more controllers which receive the images from the receiver and display the images captured by the image capturing device on the display. The endoscopic imaging system may also include a further endoscope, wherein the one or more controllers superimpose the images from the endoscope upon images from the further endoscope. Moreover, the one or more controllers determine whether the endoscope is a rear imaging endoscope and/or display an image from the endoscope as a picture in picture (PIP) image.

According to yet a further aspect of the present application, there is disclosed an endoscope including: a rigid section having opposed first and second ends and an opening situated between the first and second ends, the rigid section defining a longitudinal axis; a shaft having bifurcated ends and situated within the opening; and a base part located at the bifurcated ends, wherein a displacement of the bifurcated ends towards one another causes a rotation of the base part. The endoscope may further include one or more of an image capture device which can capture an image and a reflective element. The image capture device may include a charge coupled device (CCD) or complimentary metal oxide semiconductor (CMOS) array which may capture video images. Further, the image capture device may capture 2D and/or 3D images. Further, the rotation of the base part causes a change in a viewing direction of the image capture device. The endoscope may further include first and second scissor-type handles suitable for grasping by a user. According to the present system, at least one of the first and second scissor-type handles may be coupled to the shaft.

Further, according to the present system, there is disclosed a rigid endoscope having a rigid body portion and which may include one or more of a reflective optical component, a lighting source, and an image-capture device (e.g., a camera, a CMOS array, a CCD array, etc.), for providing a view of an operating area which may hereinafter be referred to as a surgical field. The endoscope may include a transmitter which can transmit image information obtained via the camera using a wired or wireless link. A receiver may receive the image information and send the image information to a central processing unit. The central processing unit may process the received image information as well as other image information (e.g., from another endoscope) and may output corresponding images on a display. The transmitter may include a wired electrical or optical (e.g., fiber optic) link for transmitting image information for display on a display. The transmitter may be located at a portion of the endoscope such that it does not interfere with anatomical features. Further, the size and shape of those portions of the endoscope which must pass through an opening (e.g., an incision, a natural orifice, etc.) should be such that the endoscope may pass through the opening with ease. Accordingly, in one embodiment, the diameter of a shaft or body portion of the endoscope may be less than, or equal to, about four millimeters. The endoscope may include a focal plane array which is located at a distal portion of the endoscope. This distal end portion may be rotated from about 0 through 90 degrees with respect to a longitudinal axis of an elongated portion (which may also be referred to as a shaft, body, main portion, etc.) of the endoscope. A mechanism for causing the rotation of the distal end portion may include a scissor-type handgrip such as is used in a conventional endo-scissor. By utilizing common features, the time required to train a user to operate an endoscope according to the present system may be reduced. Further, the time required to switch endoscopes, e.g., from one endoscope to another, as is often done during surgery, can be reduced. Further, by conveniently providing a rear view image of an operating field, the quality of service provided by a professional such as, for example, a surgeon, may be enhanced. Further, one or more parts or components of the present system may be suitable for various sterilization methods such as, for example, an autoclave sterilization method, if desired.

Further areas of applicability of the present system will become apparent from the detailed description provided hereinafter. It should be understood that the detailed description and specific examples, while indicating exemplary embodiments of the systems are intended for purposes of illustration only and are not intended to limit the scope of the invention.

These and other features, aspects, and advantages of the apparatus, systems and methods of the present invention will become better understood from the following description, appended claims, and accompanying drawing where:

Figure 13B:
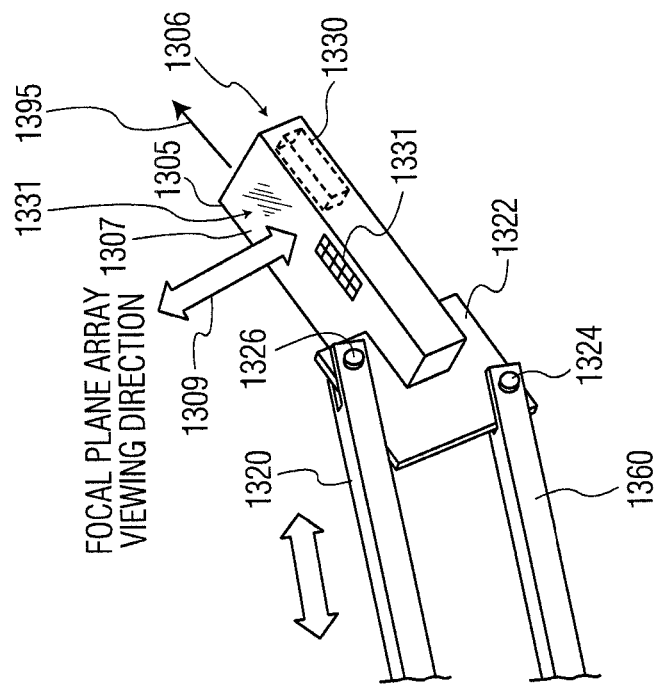
FIG. 13A is a perspective view of an endoscope according to another embodiment of the present system.
Figure 13A:
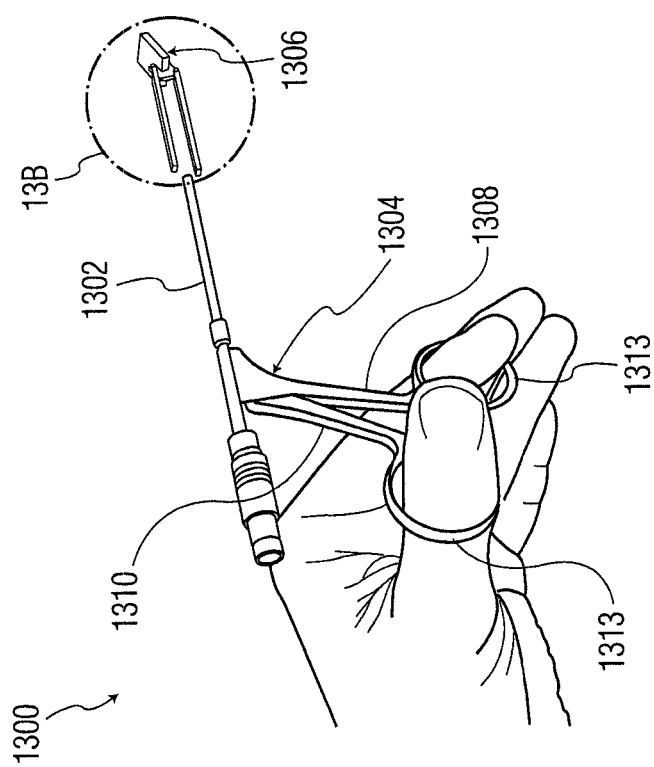
Figure 13C:
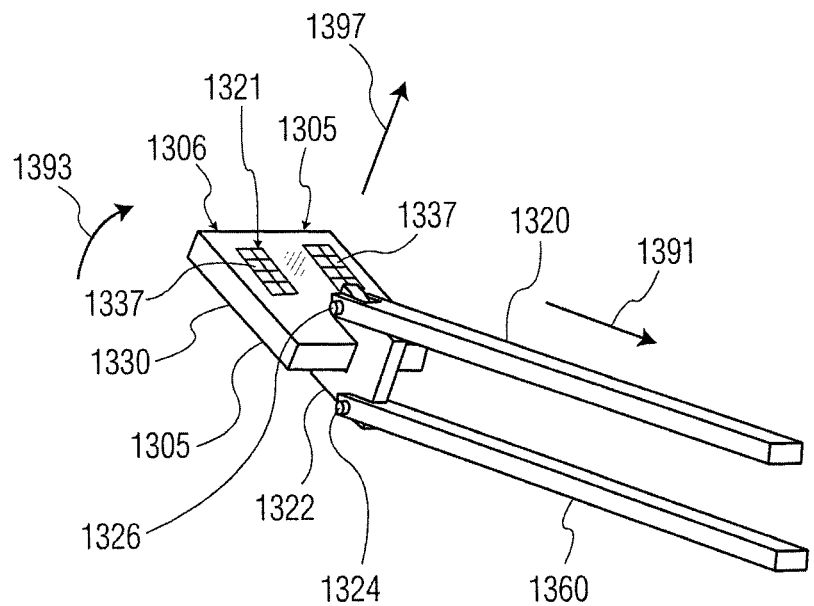
Figure 13D:
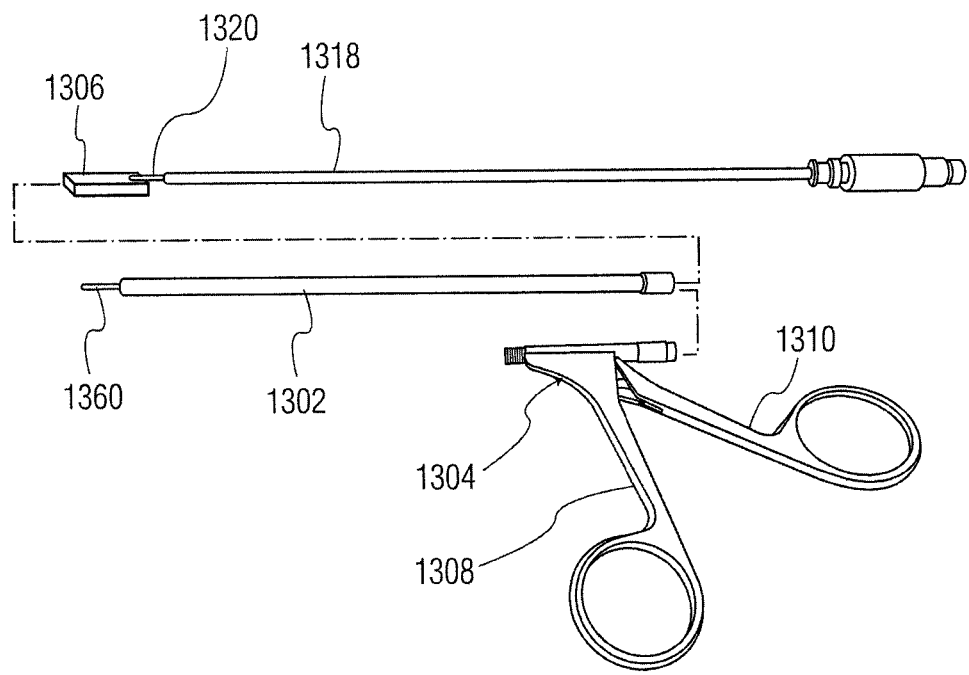
Figure 14C:
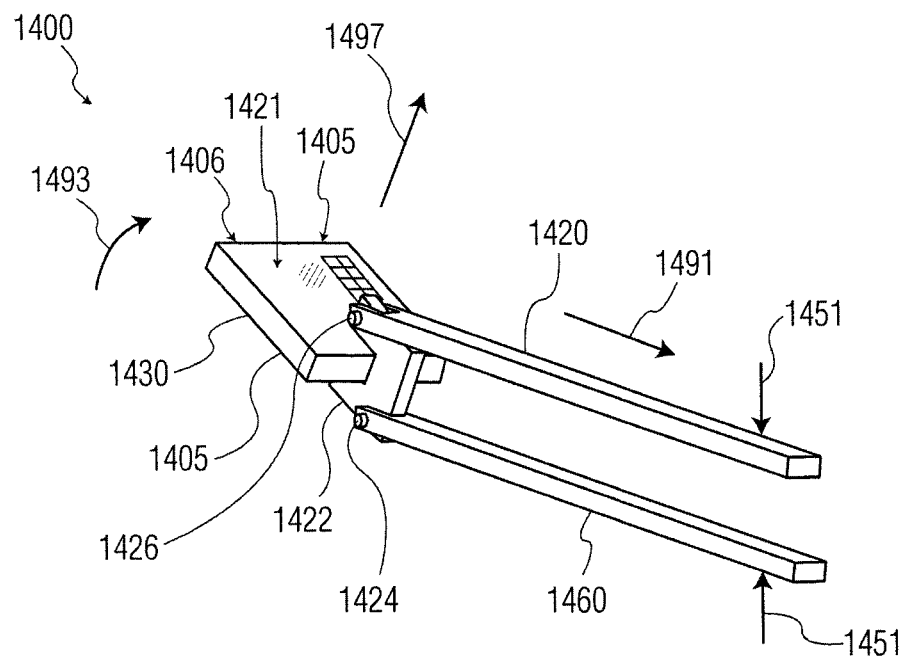
Figure 14D:
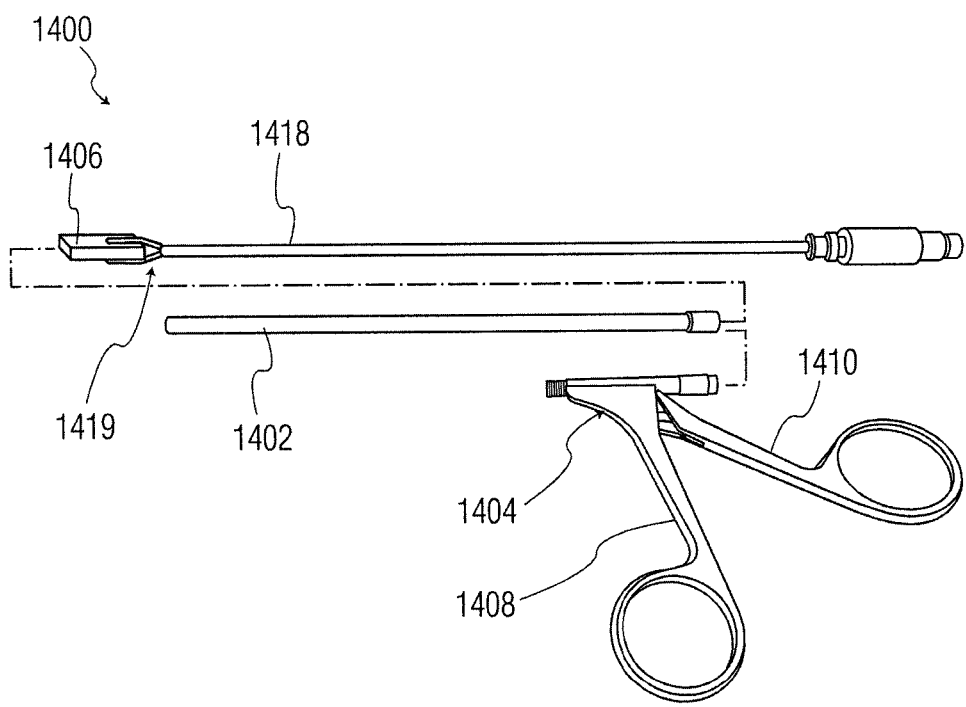
Figure 14E:
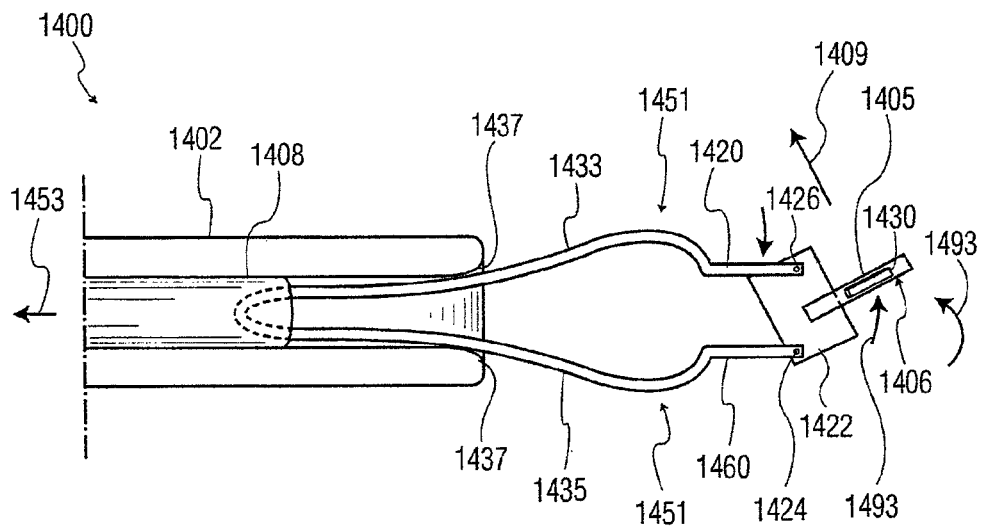
Figure 14F:
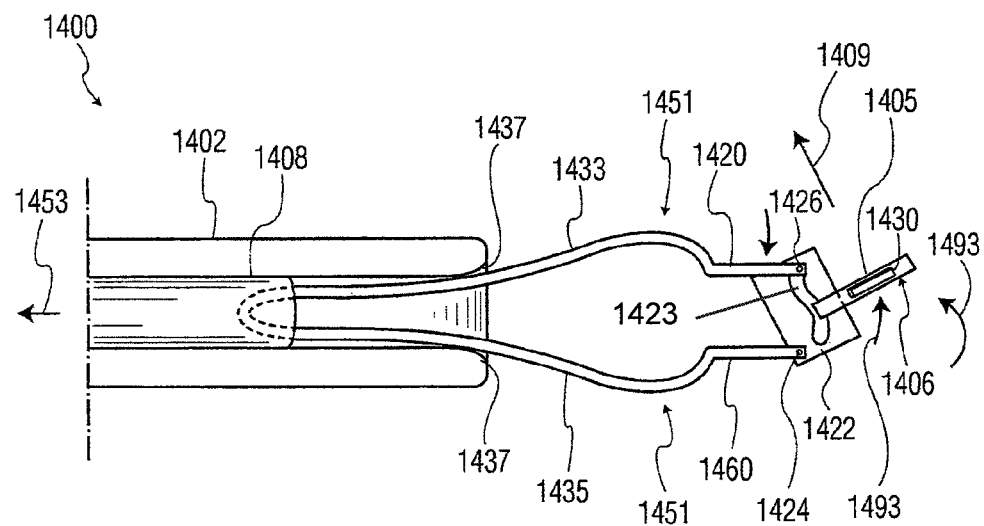

FIG. 13B-13C each illustrate a detailed view of a distal end of the endoscope shown in FIG. 13A;

FIG. 13D is an exploded view of a distal end of the endoscope shown in FIG. 13A;

FIG. 14A is a perspective view of an endoscope according to another embodiment of the present system;

FIGS. 14B-14C each illustrate a detailed view of a distal end of the endoscope shown in FIG. 14A;

FIG. 14D is a partially exploded view of a distal end of the endoscope shown in FIG. 14A;

FIG. 14E is a detailed partial cutaway view of an end portion of the endoscope shown in FIG. 14A; and FIG. 14F is a detailed partial cutaway view of an end portion of an alternative embodiment of the endoscope shown in FIGS. 14A-14E.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system.

The following detailed description is therefore not to be taken in a limiting sense, and the scope of the present system is defined only by the appended claims. The leading digit(s) of the reference numbers in the figures herein typically correspond to the figure number. Moreover, for the purpose of clarity, detailed descriptions of certain features will not be discussed when they would be apparent to those with skill in the art so as not to obscure the description of the present system.

Figure 1A:
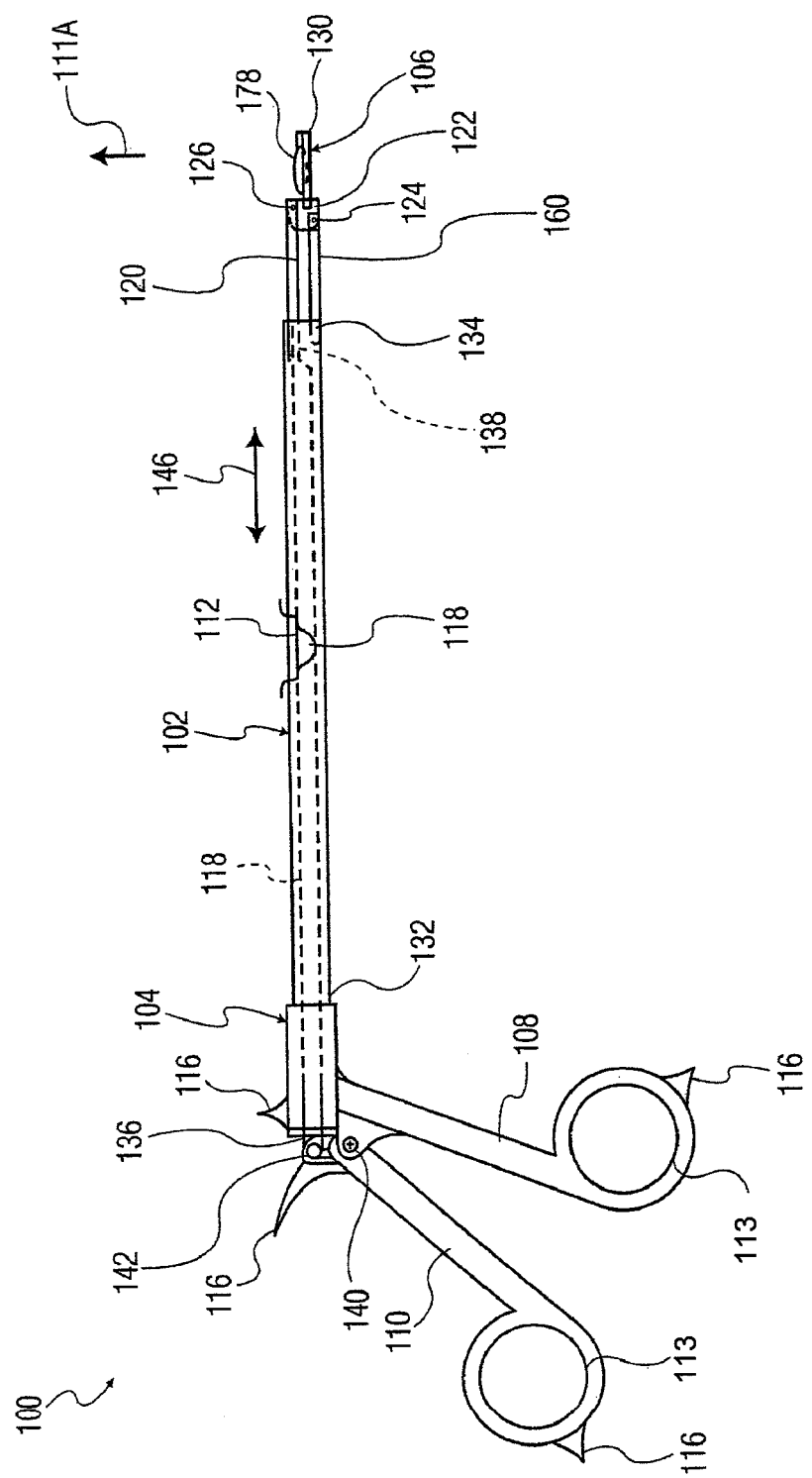
FIG. 1A is a partial cutaway side view of an embodiment of the endoscope according to the present system.

In one embodiment, there is provided system, apparatus, device, and/or method for systematically viewing a surgical field which may include an organ using a rear viewing endoscope so as to standardize endoscopy procedures which may reduce surgical time. Accordingly, medical costs and operating time may be reduced, and quality of care may be enhanced, A side view of an embodiment of the endoscope according to the present system is shown in FIG. 1A. An endoscope 100 according to the present system may include one or more of an elongated section (or barrel section) 102, a handle portion 104, and a distal portion 106.

The handle portion 104 may include first and second grip portions 108 and 110, respectively, each of which may be suitable for grasping by a user and which may include one or more grip openings 113 suitable for receiving a user's fingers. Extension parts 116 may be included to aid in gripping the first and/or second grip portions 108 and 110, respectively.

The first and second grip portions 108 and 110, respectively, may be operatively coupled (hereinafter, for the sake of clarity, coupled or attached) to each other using, for example, a hinge 140. The hinge 140 may include one or more pins, threaded rods, flexible elements, or other suitable elements as are known in the art. For example, the hinge 140 may include a simple joint or may include a compound joint. The compound joint may include a plurality of pivoting arms, pins, flexible elements, or other suitable elements as is known in the art. The first and second grip portions 108 and 110, respectively, may be biased relative to each other using a suitable biasing means such as, for example, a spring, etc., that may be coupled to one or more of the first and second grip portions 108 and 110, respectively. Thus, the first and second grip portions 108 and 110, respectively, may be biased in a predetermined position. For example, as shown FIG. 1A, the first and second grip portions 108 and 110, respectively, may be biased away from each other.

The second grip portion 110 may include proximal and distal ends 141 and 142, respectively. The proximal end 141 of the second grip portion 108 may include the grip opening 113 and the distal end 142 may include a driving part 142.

The elongated section 102 may include proximal and distal portions 132 and 134, respectively and a channel such as an opening 112 which extends along a longitudinal length thereof. The opening 112 of the elongated section 102 may be shaped and sized so as to receive a shaft 118. The shaft 118 may have one or more ends such as first and second ends 136 and 138, respectively. The shaft 118 may include an extension portion 120 which may be coupled to a distal portion 138 of the shaft 118. The extension portion 120 may include an adjusting mechanism for adjusting its position relative to the distal portion 138 of shaft 118.

The handle portion 104 may be coupled to the elongated section 102 such that the handle portion 104 or parts thereof, such as, for example, the first grip portion 108, remain stationary with respect to the elongated section 102 during use. The shaft 118 may be coupled at its first end 136 to the driving part 142 of the second grip portion 110 such that movement of the second grip portion 110 relative to the first grip portion 108, causes a transverse displacement of the shaft 118 as indicated by arrow 146.

The elongated section 102 may also include a fixing member 160. The fixing member 160 may be coupled to the distal portion 134 of the elongated section 102. The fixing member may be coupled to the distal portion 134 using any suitable method (e.g., a threaded fastener, a friction fit, a cam, etc.). The fixing member 160 may include an adjustment mechanism (e.g., a threaded screw such as a turnbuckle, etc.) to adjust the position of the fixing member 160 relative to the elongated section 102 or may adjust the length of the fixing member 160. For example, that the fixing member 160 may include a threaded end that may engage a corresponding thread in the elongated section 102 so as to adjust the location of the fixing member 160 relative to the elongated section 102. In yet other embodiments, the adjusting mechanism may include a threaded mechanism such as, for example, a collar which may adjust the location of the fixing member 160 relative to the elongated section 102.

The endoscope 100 may also include a locking mechanism to lock one or more of the first and second grip portions 108, 110, respectively, in position relative to the other. The locking mechanism may also lock the shaft 118 relative to the elongated section 102. Suitable locking mechanisms may include, for example, cam, friction, and/or pawl based locking mechanisms.

The distal portion 106 may include one or more of a base 122 and an image acquisition device 130. The base 122 may be coupled to one or more of the fixing member 160 and the extension portion 120 using any suitable method such that the base 122, or parts thereof, may rotate relative to the extension portion 120 and/or the fixing member 160. Accordingly, the base 122 may be coupled to the fixing member 160 using, for example, at hinged such as, a pivot 124 and may be coupled to the extension portion 120 at a pivot 126. Pivots 124 and/or 126 may include a fastener such as a pin or other suitable fixing members. In other embodiments, it is envisioned that the fastener may include a pin, a rivet (or other deformable connector), a screw, a bolt (or other threaded connector), a pin, a flexible member (e.g., a polymer or spring), etc.

The image acquisition device 130 may include any suitable device for capturing video and/or still images and/or transmitting these captured images. Accordingly, the image acquisition device may, include for example, one or more of a controller, a CCD array, one or more optical elements, a power source, a transmitter. The one or more optical elements may include lenses 178, prisms, mirrors, etc. In one embodiment, it is envisioned that the image acquisition device may include, for example, a focal plane array such as a thin observation module by bound optics (TOMBO) imaging system as is known in the art. In yet other embodiments, it is envisioned that the image acquisition device may include an encapsulated real-time wireless imaging apparatus. In yet other embodiments, it is envisioned that the image acquisition device may include, for example, a digital imaging camera such as, for example, a CCD array. However, regardless of the type of image acquisition device that is used, the device should be configured and arranged such that the images corresponding with a rear view (e.g., corresponding with a rearward field of view) of a surgical field may be obtained when, for example, one or more of the first and second grip portions 108 and 110, are situated in a predetermined region relative to each other. The image acquisition device 130 may be white balanced when desired.

Although a wireless image acquisition device is described, it is also envisioned that the image acquisition device may include a wired wireless transmission system which may transmit acquired images using an electrical connection and/or a fiber-optic link.

Figure 1B:
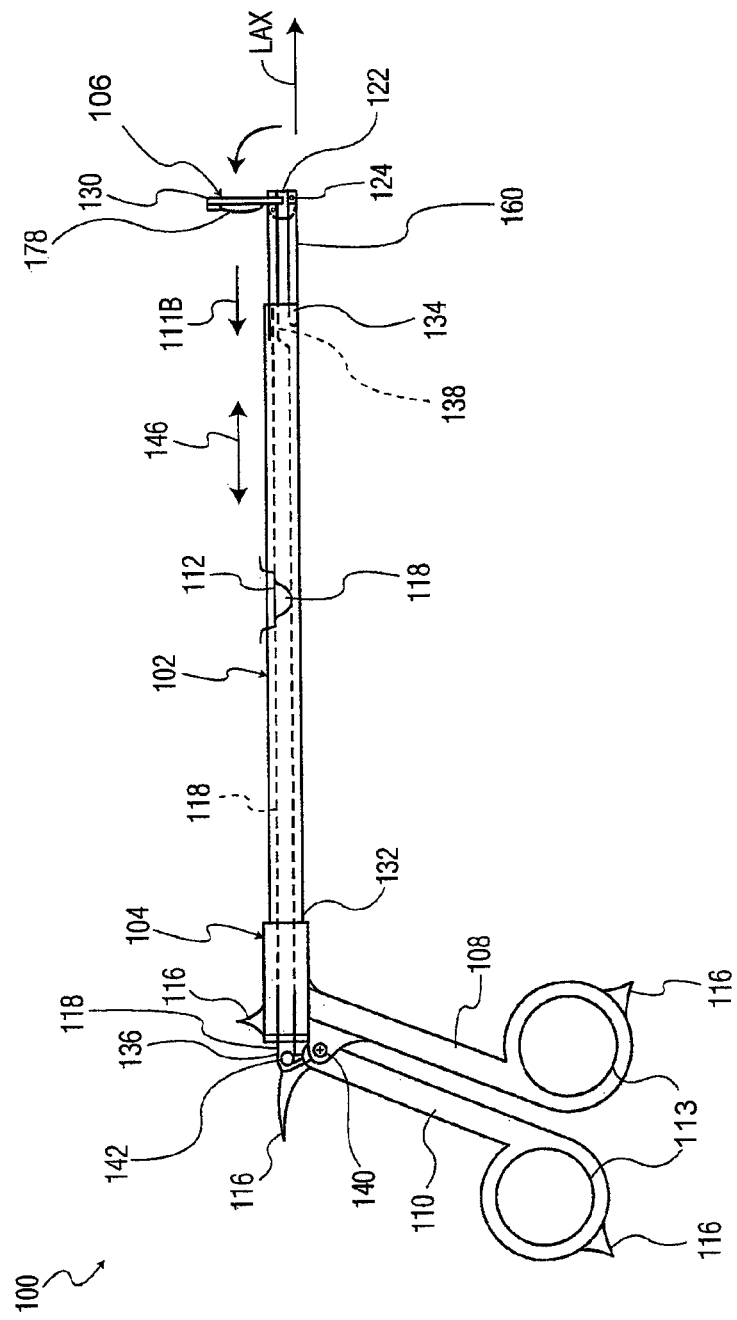
FIG. 1B is another a partial cutaway side view of the endoscope shown in FIG. 1A.

Another side view of the endoscope shown in FIG. 1A is shown in FIG. 1B. The second grip portion 110 is shown in a depressed position. When the second grip portion 110 is depressed, a displacement force may be transmitted to the base 122 via the shaft 118. Accordingly, this displacement force (e.g., as indicated by arrow 147) may cause the rotation of the base 122 about pivot 124 so as to change a viewing direction of the image acquisition device 130 as illustrated by arrow 111B (c.f., arrow 111A as shown in FIG. 1).

Figure 2:
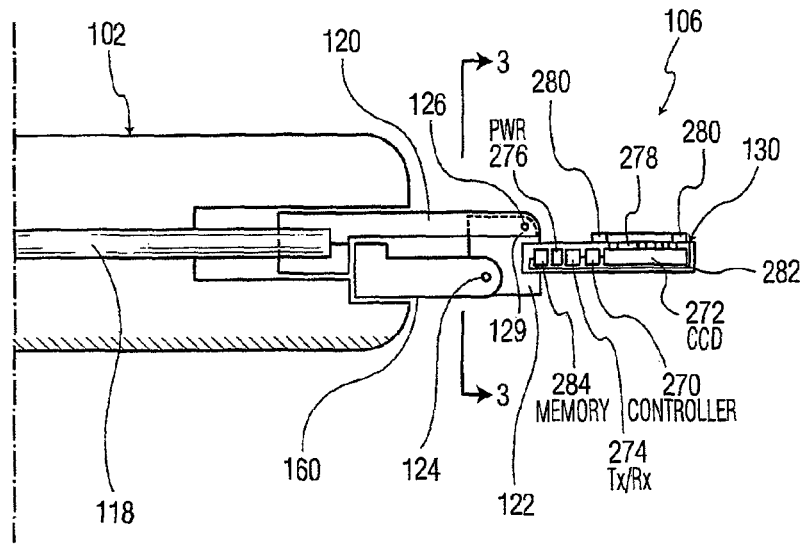
FIG. 2 is a detailed cross sectional view of the endoscope shown in FIGS. 1A-1B.

A detailed cross sectional view of the endoscope shown in FIGS. 1A-1B is shown in FIG. 2. The distal portion 106 may include an opening defining at least part of a cavity 282 for the image acquisition device 130 or parts thereof. The image acquisition device 130 may include, for example, one or more of a controller 270, a charge-coupled device (CCD) 272, a transmitter/receiver (Tx/Rx) 274, a power source 276, a memory 284, one or more light sources 280, and one or more lenses 278. Although the controller 270, the charge-coupled device (CCD) 272, the transmitter/receiver (Tx/Rx) 274, the power source 276, the memory 284, the one or more light sources 280, and the one or more lenses 278 are shown located in the distal portion 106, one or more of these components may be mounted elsewhere in the endoscope 100 according to the present system. Further other type of detectors may be used alone or in combination with the CCD 272, such as CMOS (complementary metal oxide semiconductor) image sensors.

The controller 270 may control the overall operation of the image acquisition device 130. The controller 270 may also process commands received from an external control station, etc.

The CCD 272 may include an array of CCDs and may acquire an image via the one or more lenses 278. The CCD 272 may transmit the acquired image to the controller 270. The controller 270 may then process the received image information and send the processed image information to the Tx/Rx 274

The Tx/Rx 274 may receive the image information from the controller and upconvert this information and/or transmit this information. The Tx/Rx 274 may transmit the image information using any suitable transmission method. For example, the Tx/Rx 274 may wirelessly via an antenna. The Tx/Rx 274 may also include a receiver (Rx) for receiving signals from, for example, a control station and send this information to the controller 270 for further processing.

The memory 284 may store information (e.g., image information (corresponding with captured images), operating programs or code, etc.) under the control of the controller 270. The memory 284 may include for example, one or more of a random access memory (RAM), a read only memory (ROM), a flash memory, etc.

The one or more light sources 280 may be driven by the controller 270 and may provide a light of a suitable wavelength. Thus, the one or more of the light sources 280 may include light sources such as, for example, light emitting diodes (LEDs), and may optionally provide light at different wavelengths from each other. Accordingly, pathological abnormalities may be more readily detected by, for example, the system or a user, when subject to light having a first predetermined wavelength (or wavelengths). This light may then be used to conveniently detect (e.g., by the system or a user) abnormalities such as, for example, cancerous cells. Further, the LEDs may output white light for general lighting and imaging. Accordingly, the controller 270 may control one or more of the light sources to output one or more types of light, as desired.

The power source 276 may include any source capable of providing power to the image acquisition device. For example, the optional light source 280 may include one or more batteries, capacitors, inductors (e.g., capable of generating a charge from a magnetic field in which the endoscope of the present system is located), etc. However, in other embodiments, it is envisioned an external power source may be used.

In alternative embodiments, it is envisioned that the controller 270 may also control one or more focusing devices to focus the one or more lenses either automatically or under the control of a user. Further, a user may select a type of light and transmit a corresponding command (e.g., via a control unit) to the controller 270.

Figure 3:
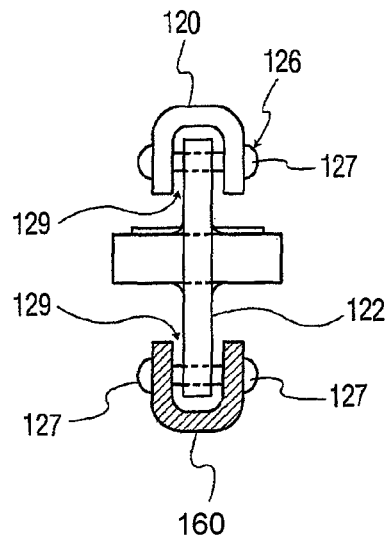
FIG. 3 is a view of the endoscope taken along lines 3-3 of FIG. 2.

A view of the endoscope taken along lines 3-3 of FIG. 2 is shown in FIG. 3. The base 122 may be attached to either or both of the fixing member 160 and the extension portion 120 using, for example, pins 127 which are placed through corresponding holes in the base 122, the fixing member 160, and the extension portion 120. One or more openings 129 may be shaped and sized (e.g., oversize, oblong, etc.) such that undesirable flexing of the base 122, the extension portion 120, and/or the fixing member 160 may be reduced or entirely prevented when the base 122 is rotated relative to the fixing member 160.

Figure 4A:
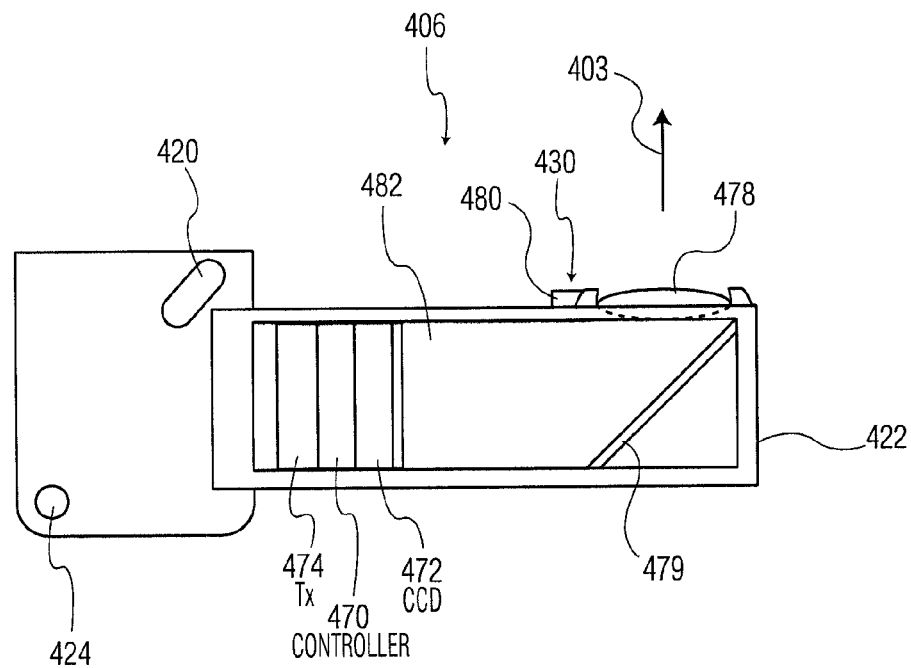
FIG. 4A is a side view of a distal portion of the endoscope according to another embodiment of the present system.

A side view of a distal portion of the endoscope according to another embodiment of the present system is shown in FIG. 4A. Distal portion 406 may include an image acquisition device 430 which may be enclosed in at least part of a cavity 482 within a base 422. The image acquisition device 430 may include one or more of a CCD 472, a controller 470, a transmitter (TX) 474, one or more optical elements, a memory, a light source 480, and a power source. The CCD 472 may have an imaging plane which is parallel to the viewing direction as shown by arrow 403. The one or more optical elements may include, for example, a lens (or lens array) 478 and/or a prism (or mirror) 479. The one or more optical elements may be situated apart from the CCD 472 so as to attain a proper focal length. The light source 480 may be controlled by the controller 470 and may include one or more LEDs.

Figure 4B:
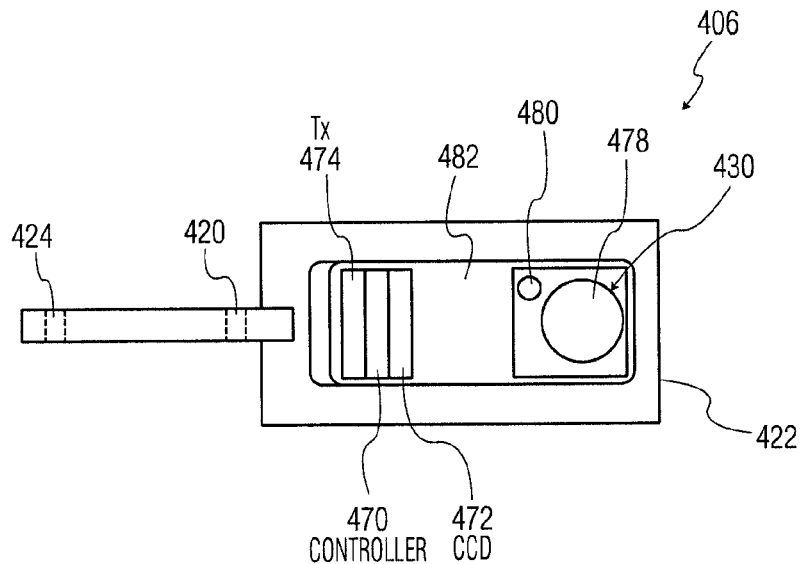
FIG. 4B is a top view of the distal portion shown in FIG. 4A.

A top view of the distal portion shown in FIG. 4A is shown in FIG. 4B. Only a single lens 478 and light source 480 are shown. However, a plurality of lenses and/or light sources may be used, if desired. Either or both of the pivot holes 420 and 424 may be oblong, etc., such that the fixing member 160 and/or the extension portion 120 may move in relation to the base 422 and, thus, reduce or prevent undue flexing during rotation of the base part 422.

Figure 5A:
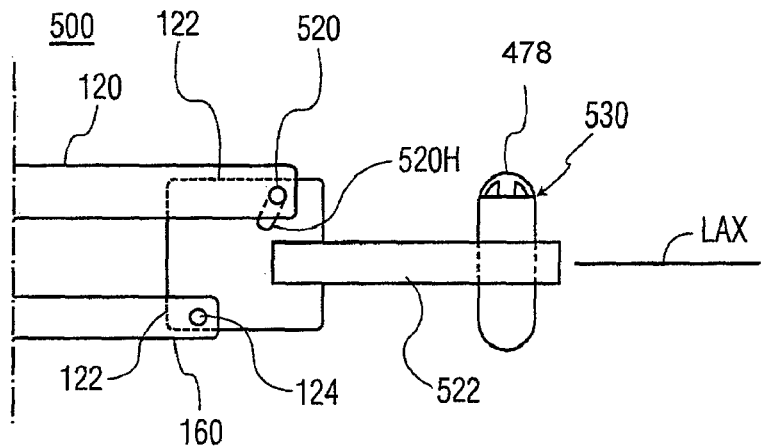
FIG. 5A is a side view of a distal portion of an endoscope according to another embodiment of the present system.

A side view of a distal portion of an endoscope according to another embodiment of the present system is shown in FIG. 5A. An endoscope 500 includes a base 522 which may be configured to hold an image acquisition device 530 in a desired position as shown. The base 522 may be hingedly attached to the fixing member 160 at, for example, pivot 124 and is attached to the extension portion 120 at pivot 520 using fixation devices such as, for example, pins, screws, rivets, etc., which be coupled to corresponding openings in the base part 522, the fixing member 160, and/or the extension portion 120. One or more of the openings in the base 522 may have an oblong shape such as 520H so that the undue flexing of the extension portion 120 and/or the fixing member 160 may be reduced or entirely prevented. Further, it is also envisioned that one or more of the openings in the base (e.g., 520) may have a cam profile which may aid rotation of the base during operation. However, it is also envisioned that the extension portion 120 and/or the fixing member 160 may flex and/or be displaced in, for example, a direction that is transverse to the longitudinal axis (LAX) of the endoscope 500. The image acquisition device 530 may include, a common off-the-shelf capsule endoscope such as is known in the art. Further, the image acquisition device 530 may include one or more light sources such as LEDs 580 for providing a source of light during use. The base may include a mounting part for mounting the image acquisition part 530 thereto.

Figure 5B:
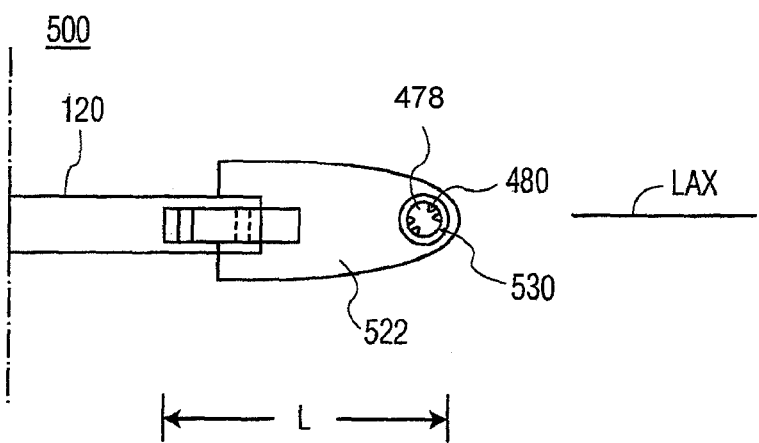
FIG. 5B is a top view of the endoscope shown in FIG. 5A.

A top view of the endoscope shown in FIG. 5A is shown in FIG. 5B. The image acquisition device 530 may be held in place in the base 522 using any suitable means. For example, a friction fit, a collar, adhesives, etc., which may be compatible with the image acquisition device 530 may be used. A length L of the base 522 should be sized such that a proper view may be acquired by the image acquisition device 530 during use.

Figure 6C:
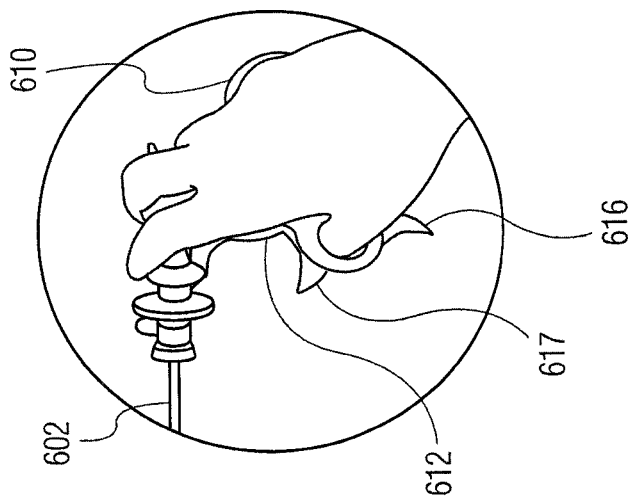
FIGS. 6A-6C are side views of an endoscope according to an alternative embodiment of the present system.
Figure 6B:
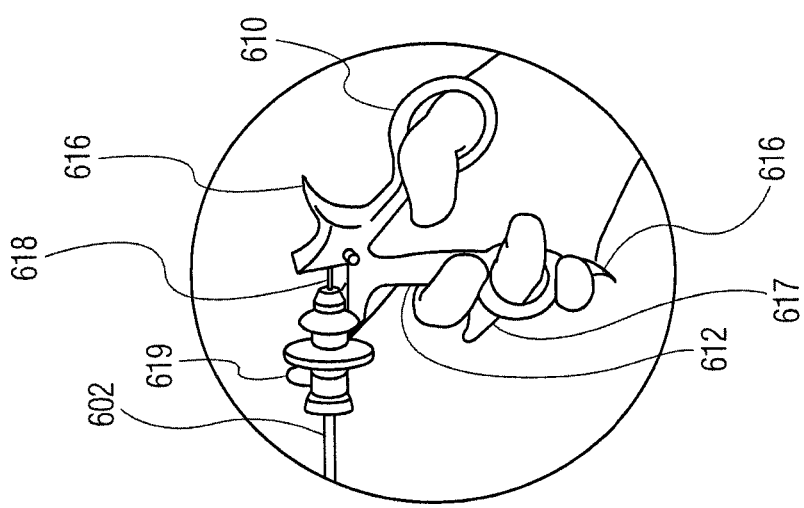
Figure 6A:
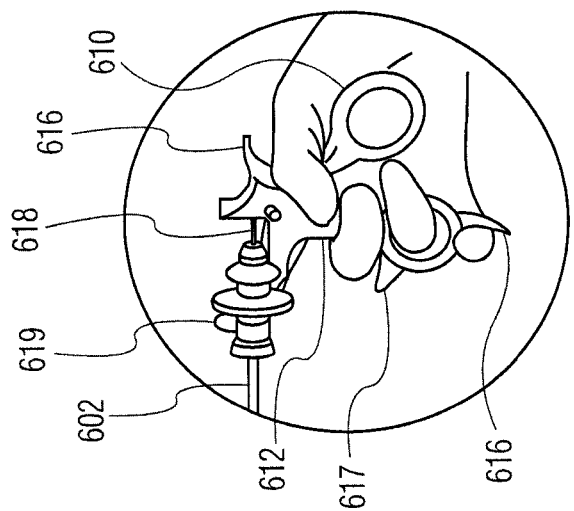

Side views of an endoscope according to an alternative embodiment of the present system is shown in FIGS. 6A-6C. An endoscope 600 may include handles which are configured for receiving a user's hand. A first grip portion 612 may be fastened to an elongated section 602. A second grip portion 610 may be pivotably coupled to the first grip portion 612 and a shaft 618 situated within the elongated section 602. Extensions 616 are situated for grasping by a user. A lever 617 operates to perform a desired function such as, for example, lock the first and second grip portions 608 and 610, respectively, in a desired position relative to each other. A lever 619 operates to provide a couple such as, for example, an electrical couple, an optical couple, etc., to an external device.

Figure 7A:
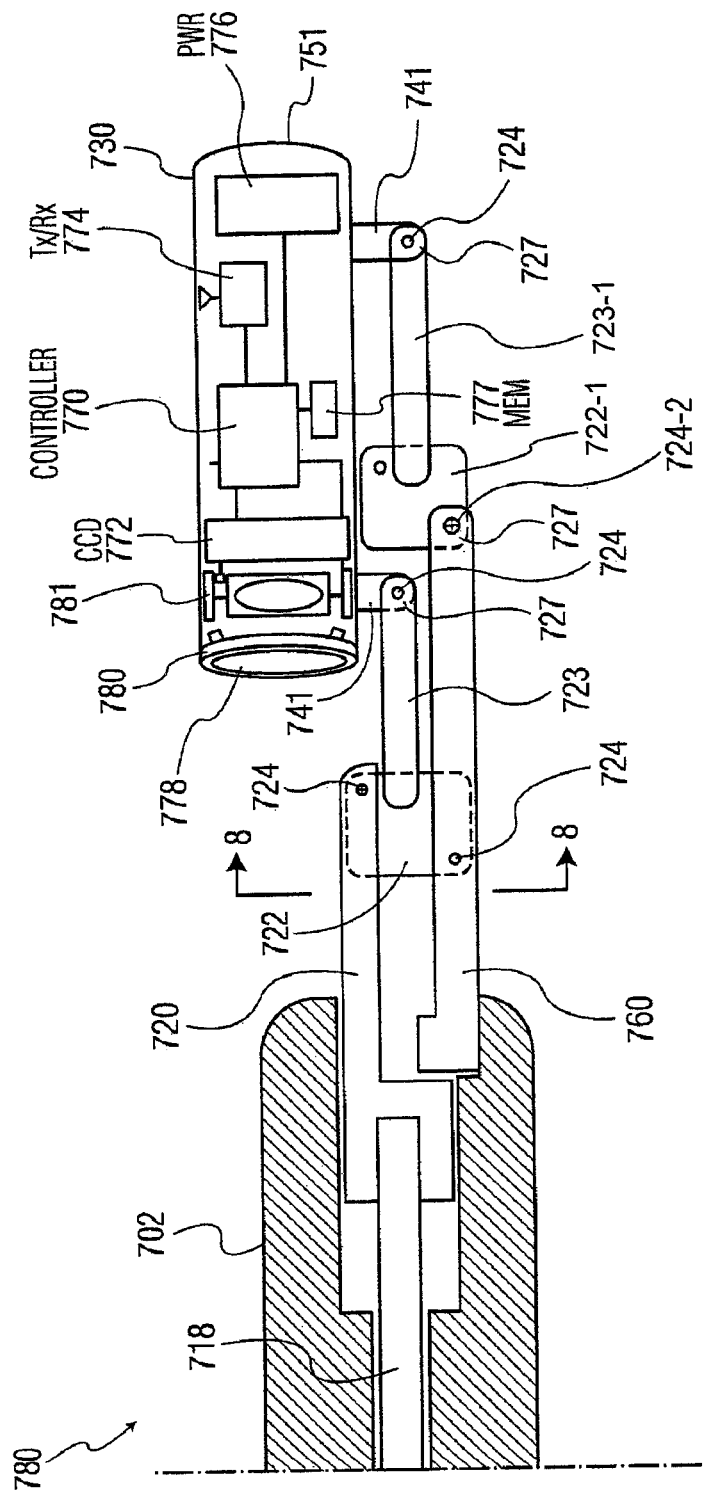
FIG. 7A is a side view of a distal portion of an endoscope according to another embodiment of the present system.

FIG. 7A is a side view of a distal portion of an endoscope according to another embodiment of the present system. An endoscope 780 is shown in a closed configuration suitable for insertion through an opening such as an incision. The endoscope includes an elongated assembly 702, a shaft 718 and an extension portion 720, which may be similar to the like parts of the endoscope shown in FIG. 1. A fixing member 760 may be attached to the elongated assembly 702 using any suitable method and may be attached to base parts 722 and 722-1 using any suitable fastening method. For example, a suitable fastening method may include a screw, rivet, and/or pin 727 which may be inserted within corresponding openings of the base parts (722 and 722-1) and/or the fixing member 760. The base parts 722 and 722-1 may include arms 723 and 723-1. An image acquisition device 730 may be attached to the base parts 722 and 722-1 using any suitable fastener. For example, the image acquisition device 730 may be attached to the arms 722 and 722-1 using a fastener such as a pin, a screw, a rivet, etc., at pivots 724 or an adhesive. Further, it is also envisioned that the fastener may be formed integrally with, for example, the arms 722 and 722-1, or the image acquisition device. In yet other embodiments, it is envisioned that the fastener may be formed from a flexible element such as a polymer with suitable characteristics.

The extension portion 720 may be coupled to one or more of the base parts 722 or 722-1 using any suitable method such that a force (e.g., from the shaft 718) may be transmitted from the extension portion 720 to a corresponding base part 722 or 722-1. For example, the extension portion 720 may be attached to the base part 722 using a pin 727 or the like. It is also envisioned that at least part of an attaching member may be formed integrally with, for example, the image acquisition device, the base parts 722 and 722-1, the extension portion 720, and/or the fixing member 760.

The image acquisition device 730 may include, for example, a body 751 defining at least a part of a cavity for containing operational components. The body 751 may include one or more mounting flanges such as, for example flanges 741 for coupling the body 751 to the arms 723 and 723-1. The operational components may include one or more of a controller 770, a CCD 772, a magnification assembly 781, one or more LEDs 780, one or more optical elements such as, for example, lens 778, a transmitter/receiver Tx/Rx 774, a power source 776, and a memory 777. The magnification assembly 781 may also be used to zoom in/out as desired. Further, focusing system may be provided. This system may be fixed, user adjustable, and/or automatic. Further, the controller may also provide a digital-type zoom.

The controller 770 may control the overall operation of the image acquisition device 730.

The one or more of the one or more LEDs 780 may be operated directly from the power source or may be controlled by the controller 770. Further, one or more of the one or more LEDs 780 may output a wavelength of light that is different from a wavelength of another LED such that two different lighting modes may be output under the control of, for example, the controller 770. The lighting modes may correspond with lighting modes which may output one or more wavelengths or spectrums which may be better able to, for example, detect abnormalities. For example, one lighting mode may correspond with an imaging optical mode, while another optical mode may correspond with a Narrow Band Imaging (NIB™) optical mode as is known in the art.

The magnification assembly 781 may operate under the control of the controller 770 and may include one or more optical elements such as lenses that may be adjusted so as to increase/decrease magnification of an image to be captured. The user may transmit commands to the system to set a desired amount of magnification.

The memory 777 may store operating code, image information, and/or other data under the control of the controller 770.

The power source 776 may include any suitable power source such as, for example, an inductive power source, a capacitor, a battery, etc. The power source may also receive power from an outside source using, for example, an electrical connection.

The Tx/Rx 774 may include a wired and/or a wireless transmitter which can transmit information which may include image information from the controller 770 and/or receive information such as, for example, operating instructions from an outside source.

Although not shown, the arms 723 and 723-1 may be shaped and sized such that they may be attached to the body portion of the image acquisition device 130 at any location on the body portion 751. Further, the image acquisition device 730 may, for example, include a conventional medical imaging capsule and/or may be compatible with high definition imaging (HD) systems. Further, an attachment such as, for example, a cradle may be used to attach an imaging capsule to the arms 723 and 723-1.

Figure 7B:
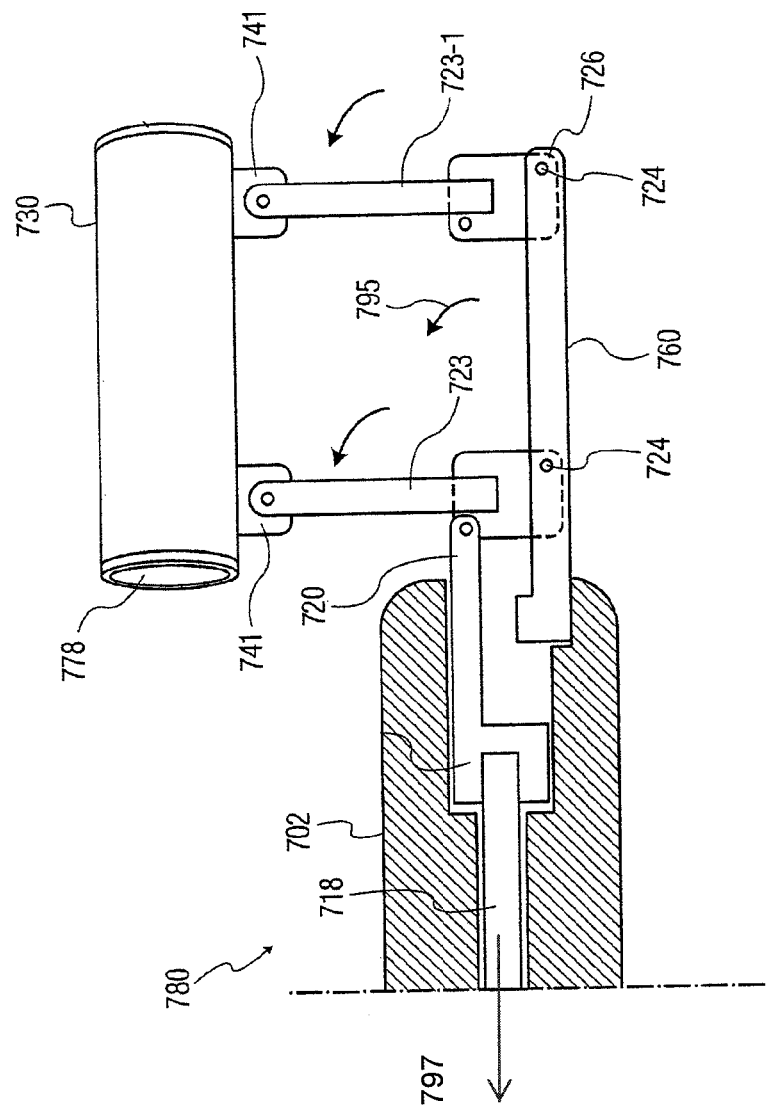
FIG. 7B is a side view of the endoscope shown in FIG. 7A in an open position.

A side view of the endoscope shown in FIG. 7A in an open position is shown in FIG. 7B. The image acquisition device 730 is shown in an elevated rear viewing position. A biasing means may be used to return the image acquisition device 730 to a seated position as is shown in FIG. 7A. To elevate the image acquisition device 730, a user may depress the second grip portion 110 towards the first grip portion 108 which may displace the shaft 718 as illustrated by arrow 797. The shaft 718 then rotates the base part 722 about pivot 724 as shown by arrow 795. As the base part 722 is rotated, the arm 723 raises the image acquisition device 730. The arms 723 and 723-1 may be shaped and sized such that a desired viewing direction may be obtained. For example, assuming that the base parts 722 and 722-1 as well as arms 723 and 723-1 have similar shapes and sizes, then as the image acquisition device 730 is raised, it will maintain a parallel rear direction of view as illustrated by arrow 763. Likewise, by changing the size of the base parts 722 and 722-1 and/or the arms 723 and 723-1, a non-parallel direction of view may be obtained at different extensions of the image acquisition device 730.

Figure 8:
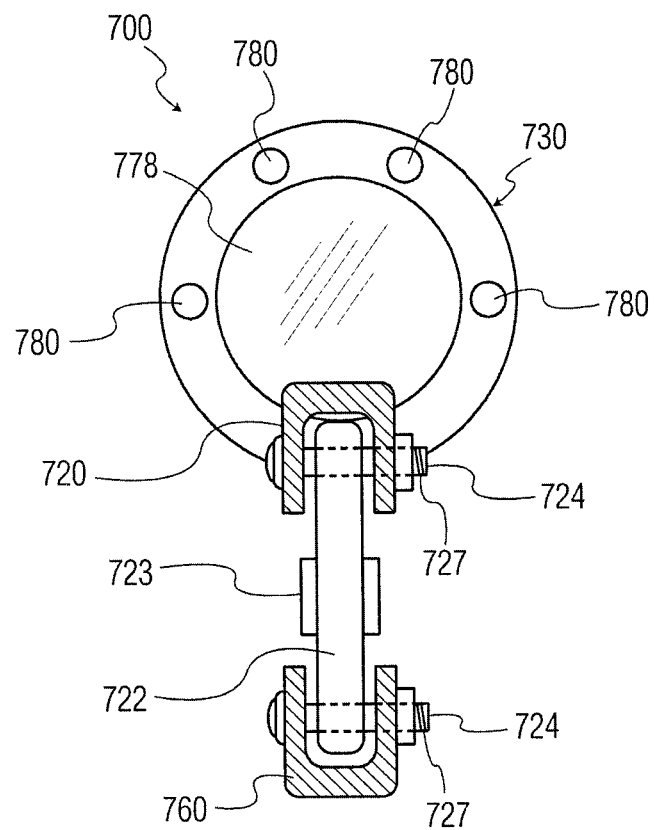
FIG. 8 is a cross sectional view of the endoscope shown in FIG. 7A taken along lines 8-8.

A cross sectional view of the endoscope shown in FIG. 7A taken along lines 8-8 is shown in FIG. 8. The one or more LEDs 780 may be situated about the lens 778.

Figure 9:
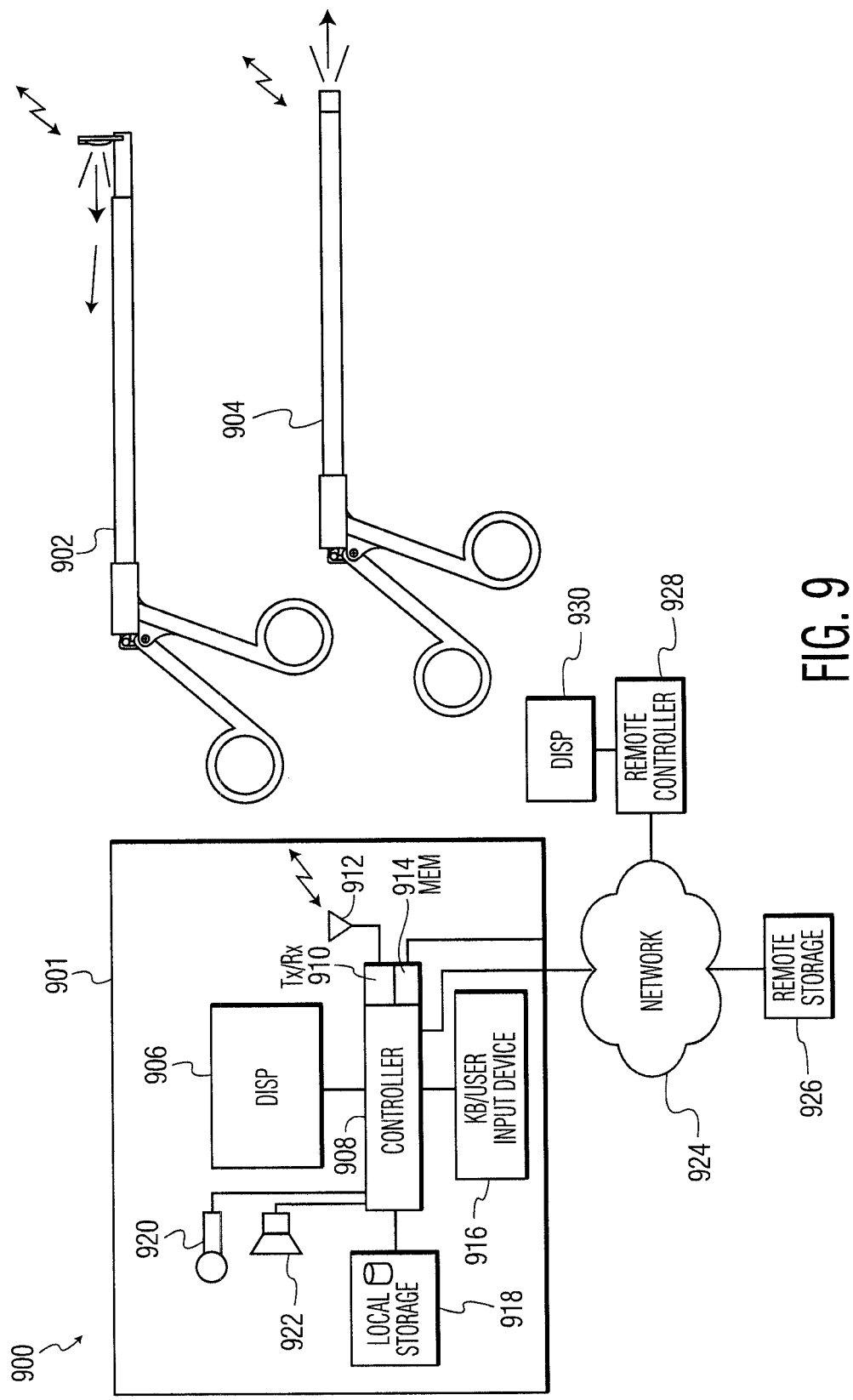
FIG. 9 is a schematic view of an endoscopic imaging system according to an embodiment of the present system.

A schematic view of an endoscopic imaging system according to an embodiment of the present system is shown in FIG. 9. An endoscope system 900 may include one or more of a rear imaging endoscope 902, a front imaging endoscope 904, a control unit 901, a controller 908, a display 906, user input device 916, a transmitter/receiver (Tx/Rx) 910, an antenna 912, a memory 914, a local storage device 918, a speaker 922, a microphone 920, a network 924, a remote display 930, a remote controller 928, and a remote storage 926.

The control unit 901 may include the controller 908 and may control the overall operation of the endoscope system 900. The controller 908 may include one or more controllers which may be located at one or more locations. The controller 908 may receive image information such as, for example, live video and/or still image information (image information) from image capture devices of one or more endoscopes such as, for example, endoscopes 902 and/or 904. The image information may be transmitted from a corresponding endoscope using a wired and/or wireless transmission scheme. Any suitable wireless transmission scheme may be used. The transmitted wireless image information may be received by the antenna 912 and then transferred to the Tx/Rx 910. The Tx/Rx 910 may then optionally downconvert the received image information and transmit this information the controller 908. The controller 908 may then further process the received image information and display this information on the display 906. The controller 908 may also process the received image information and transmit corresponding information to one or more storage devices such as, for example, storage 918 and/or 926.

The user input device 916 may include, for example, a keyboard, a touch screen, a track ball, a mouse, a pointer, or other suitable devices.

The speaker 922 may output audible sound under the control of the controller 908. The controller 906 may also employ a text-to-speech (TTS) and/or speech-to-text (STT) processing to convert corresponding text or speech to a desired format.

The microphone 920 may receive audible inputs from the user and transmit this information to the controller 908 for further processing.

The controller may use a text-to-speech and/or a speech-to-text application to perform an appropriate conversion to, for example, generate speech and/or text information that may be processed by the system. For example, a user may input an audible command such as, "lights on," which may be processed and result in the controller 908 transmitting a command to a lighting source of an endoscope such as, endoscope 902. Each endoscope 902 may have an identification (ID) that may be used to identify a command transmitted to an appropriate endoscope (e.g., 902, 904). Further, different transmission/reception frequencies may be used by each endoscope to distinguish endoscopes.

An optional Coder/Decoder (CODEC) may operatively interface the speaker 922 and/or microphone 920 to the controller 908.

The memory 914 may include for example, a random access memory (RAM), a read only memory (ROM), a flash memory, an optical memory, or other suitable memory device. The memory 914 may store operating programs and/or data generated by the controller 908.

The storage 918 may include a storage device such as, for example, a hard disc, an optical disc, a storage area network (SAN), etc. The storage 918 may operate under the control of the controller 908 and may store information such as, for example image information and associated information from the controller 908 for later use. The associated information may include, for example, one or more of user information, patient information, time information, date information, identification (ID) information, hospital information, annotations, notes, user preference information, report information (e.g., generated patient reports), etc. The storage 926 may also store programs and/or image information and associated information and provide this information to the controller 908.

The display 906 may include one or more suitable displays such as, for example, liquid crystal displays (LCDs), etc.

The controller 908 may communicate with other devices such as, for example, the controller 928 and/or storage device 926, which may be located at one or more remote locations, via the network 924 accessible via, for example, the network 924.

The network 924 may include for example, a local area network (LAN), a wide area network (WAN), a proprietary network, a system bus, in intranet, the Internet, etc. The controller 908 may communicate with the network 924 using any suitable transmission scheme.

The controller 928 may input user information via, for example, the user input device 928 and/or may output information via the display 930, the speaker 922, etc.

The storage 926 may receive information such as image information and associated information from the controller 908 and may store this information for later use. The associated information may include, for example, one or more of user information, patient information, time information, date information, identification (ID) information, hospital information, annotations, notes, etc. The storage 926 may also store programs and/or provide stored information to the controller 908.

The controller 908 may receive user inputs via one or more user input devices such as, for example, keyboard (KB) 916, the microphone 920, etc.

The remote controller 928 and/or display 930 may include similar functionality as the controller 908 and display 906, respectively. The controller 928 may interface with user input devices so as to receive user inputs at one or more locations.

Figure 10:
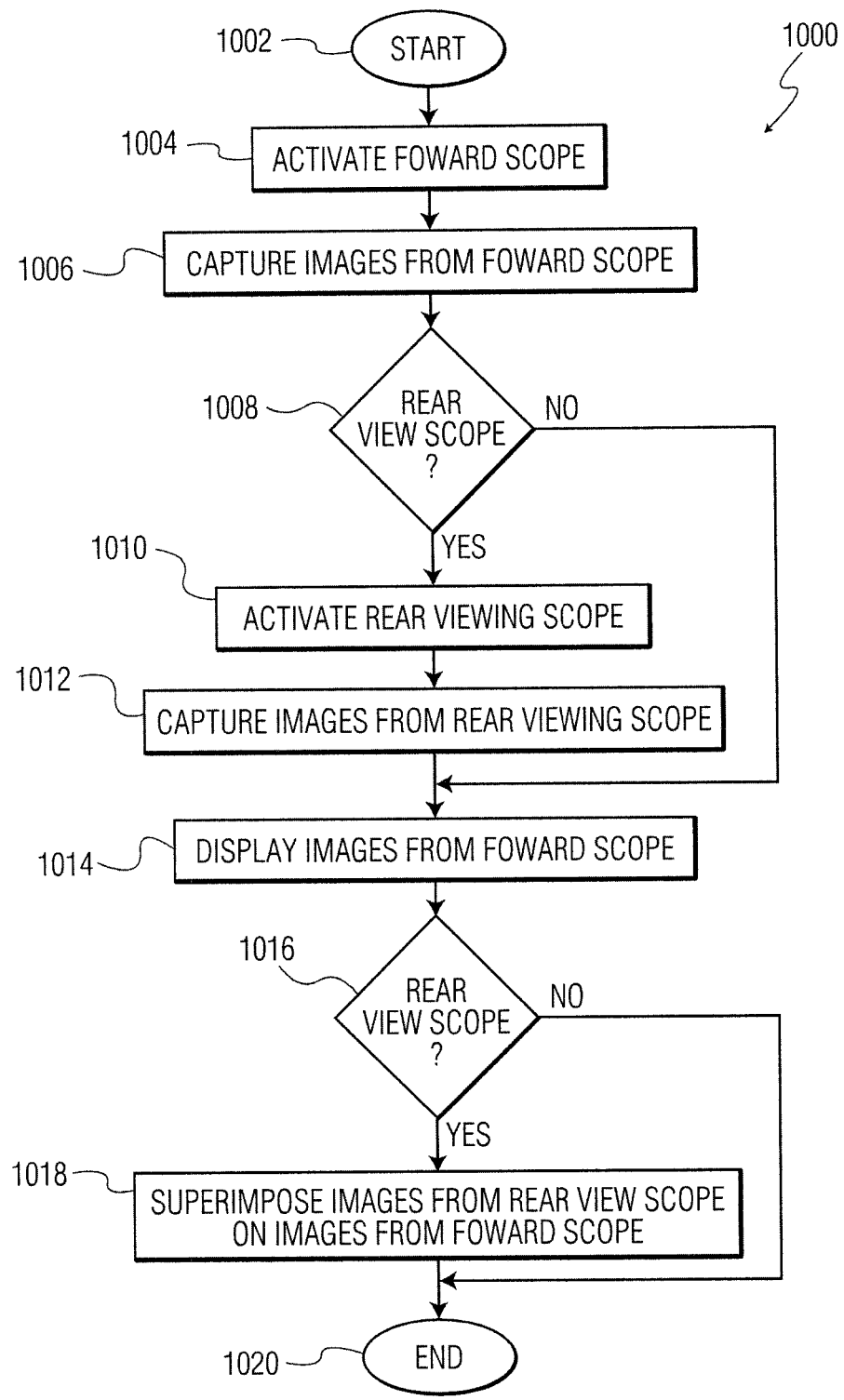
FIG. 10 is a flow chart of a process performed according to an embodiment of the present system.

A process for capturing images according to the present system will now be described. A flow chart of a process performed according to an embodiment of the present system is shown in FIG. 10. A process 1000 may be controlled by one more computers communicating directly and/or over a network and may include one or more of the following steps, acts or operations. Further, one or more of these steps, acts, or operations may be combined and/or separated into sub-steps, sub-acts, or sub-operations, if desired.

In act 1002, a process for acquiring imaging information is activated. Thereafter, the process continues to act 1004.

In act 1004, the process may activate an optional frontal imaging device such as, for example, a front viewing or main endoscope. The process may then continue to act 1006.

In act 1006, the process may capture images such as, for example, still and/or video images from the main endoscope (e.g., in real time). The process may then continue to act 1008.

In act 1008, the process may determine whether a rear-viewing endoscope is present. This decision may be base upon, for example, whether the rear-viewing endoscope is selected by a user, is present, is activated, or is otherwise to be used for obtaining images during a routine). If the process determines that rear-viewing endoscope is present, the process continues to act 1010. However, if it is determined that a rear-viewing endoscope is not present, the process continues to act 1014.

In act 1010, the rear viewing endoscope may be activated. For example, a camera of the rear-viewing endoscope may be activated so as to conserve system resources. This act may also wait for a user's input so as to conserve system resources such as, for example, battery power. The process then may continue to act 1012.

In act 1012, the process captures images such as, for example, still and/or video images in, for example, real time, from the rear-viewing endoscope. The process may then continue to act 1014.

In act 1014, the process may display the image from the main endoscope. The process may then continue to act 1016.

In act 1016, the process may determine whether it is receiving images from the rear-viewing endoscope. If the process determines that it is receiving images from the rear-viewing endoscope, the process may continues to act 1018. However, if it is determined that the process is not receiving images from the rear-viewing endoscope, the process may continue to act 1020. Alternatively, act 1016 may use a determination that is similar to the determination in act 1008. For example, the process may determine whether a rear-viewing endoscope is present (e.g., is to be used, is present, is selected by a user, etc.). If the process determines that rear-viewing endoscope is present, the process may then continue to act 1018. However, if it is determined that a rear-viewing endoscope is not present, the process may continue to act 1020.

In act 1018, the process may display the image images from the rear-viewing endoscope adjacent to, or upon (e.g., by superposition), images from the main endoscope. For example, the process may user a picture-in-picture (PIP) mode to display the images from the rear-viewing endoscope in a portion of the screen which displays the image from the main endoscope. The process may also present the user with an option to reverse, move, and or resize the images. Further, identification information may be displayed to identify the image so that the user can readily identify the image with a corresponding endoscope. If a touch screen is used, the process may receive a user's input via the display and can for example, drag images (e.g., the PIP image) to a new location, reverse the main image (primary image) and the PIP image by, for example, double clicking the main image or the PIP image. Further, the system may also recognize voice commands such as, for example, "reverse images" which may be processed by the system and result in the reversal of the main image and the PIP image. Further, the system may recognize commands such as, for example, a magnification command, a mode change command (e.g., one lighting mode to another), a picture record command, a picture replay command (e.g., corresponding to a past time e.g., "replay two minutes ago"). Further, the system may recognize a user's request to remove the PIP either temporarily or permanently. Accordingly, a surgeon may easily review past information, change screens, magnification, lighting, etc., during surgery.

In act 1020 the process may end.

However it is also envisioned that two or more screens may be used for display images from corresponding endoscopes, as desired.

Figure 11B:
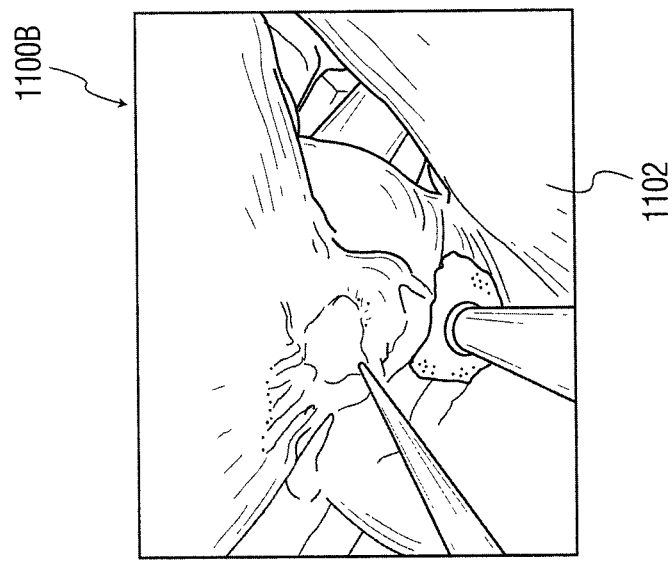
FIG. 11B is a screen shot of an image display according to the present system.
Figure 11A:
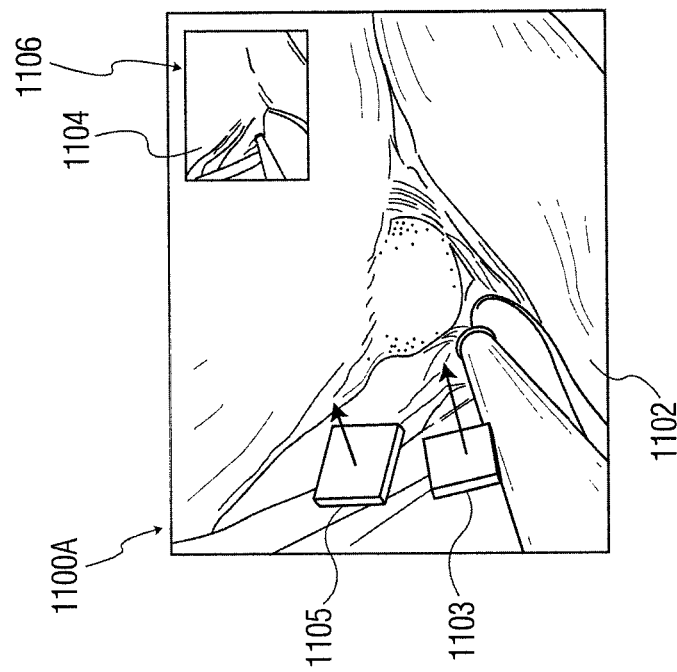
FIG. 11A is a screen shot of an image display according to the present system.

A screen shot of an image display according to the present system is shown in FIG. 11A. Screen shot 1100A may include, for example, an image 1102 such as, a still or a video image, from a first scope (e.g. a main scope). An image such as, a still or video image, from a secondary (e.g., a rear-viewing endoscope) may be displayed as a PIP 1104. The system may reverse primary (e.g., image 1102) and the secondary (image 1104) images upon the request of a user. An identifier such as a highlighted frame 1106 (e.g., a blue highlighted frame) may be used to identify the image from the secondary endoscope. For example, an image from a rear-viewing (or secondary) endoscope may be highlighted using a first color (e.g., a blue frame 1106) and/or an image from a forward-viewing (or main) endoscope may be identified using a highlight of a different color. The image acquisition devices according to the present system may include a stereoscopic viewing system that may display captured images (e.g., video images) in stereovision. The system may also determine an orientation of the image acquisition device of the rear-viewing endoscope and display this information (e.g., by superposition) as illustrated by the flat planes 1103, 1105 and corresponding arrows which may illustrate an image plane of a rear viewing endoscope within the primary image 1102 for a user's convenience.

A screen shot of an image display according to the present system is shown in FIG. 11B. Screen shot 1100B illustrates an image in which an endoscope is inserted at an angle to remove a meningioma attached behind a tumor. In particular, FIGS. 11A and 11B illustrate an endoscopic resection of a Meningioma brain tumor and its gradual dissection of the optic nerves where, in addition to a surgical tool (e.g., for dissection), a rear-viewing endoscope according to the present system may be inserted to provide various views, e.g., a rear view, of the tumor.

Figure 12A:
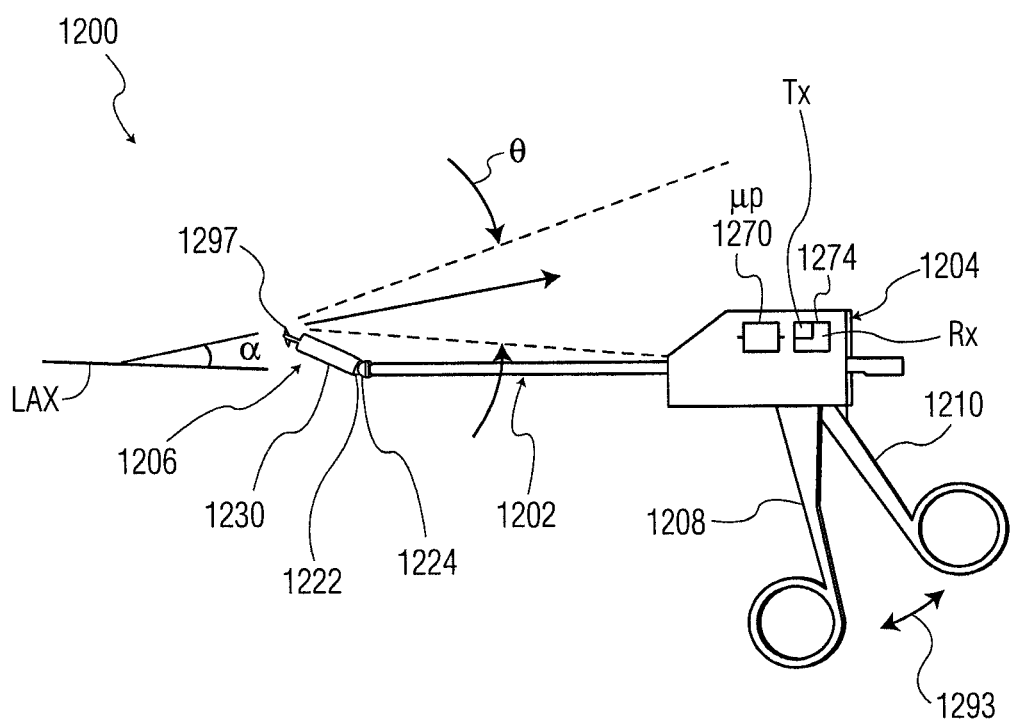
FIG. 12A is a side view of another endoscope according to another embodiment of the present system.

A side view of another endoscope according to another embodiment of the present system is shown in FIG. 12A. An endoscope 1200 may include one or more of an elongated section 1202, a handle portion 1204, and a distal portion 1206.

The elongated section 1202 includes may be coupled to the distal portion 1206 at one side and may be coupled to the handle portion 1204 at another side. The elongated section may have an opening through which a shaft 1218 passes.

The handle portion 1204 may include one or more of first and second scissor-type handles 1208 and 1210, respectively. The first scissor-type handle 1208 may be coupled in a fixed position relative to the handle portion 1204 while the second scissor-type handle 1210 may be coupled in a movable position relative to the handle portion 1204. Accordingly, the second scissor-type handle 1210 may move towards and/or away from the first scissor-type handle 1208 as illustrated by arrow 1293. The handle portion 1204 may include one or more of a controller 1270, a transmitter receiver (Tx/Rx) 1274, a memory, and a user input device for inputting a user's command. The controller 1270 may control the overall operation of an image acquisition device 1230. The Tx/Rx 1274 may transmit image information from the controller via a wired and/or wireless link.

The distal portion 1206 may include a base 1222 and an image acquisition device 1230 coupled thereto. The base 1222 may be coupled to the elongated section 1202 via a hinge 1224. The base 1222 may be coupled to the second scissor-type handle 1210 via the shaft 1218 such that displacement of the second scissor-type handle 1210 displaces the base 1222 and therefore the image acquisition device 1230 relative to a longitudinal axis (LAX) of the endoscope 1200.

The image acquisition device 1230 may include one or more of optical elements (e.g., lenses, reflectors, prisms, mirrors, etc.), magnification devices, and a CCD. The CCD may transmit image information to the controller 1270. The optical elements may include a distal optical element 1297 which may include for example, a reflector such as, a mirror which may be used to adjust at least part of an imaging direction of the image acquisition device 1230. By adjusting the angle of the image acquisition device 1230 relative to the LAX and adjusting an angular position of the distal optical element 1297 relative to a longitudinal axis of the image acquisition device (LX), an imaging direction a with respect to the LAX may be adjusted. The image acquisition device 1230 may also have field of view θ as shown.

Figure 12B:
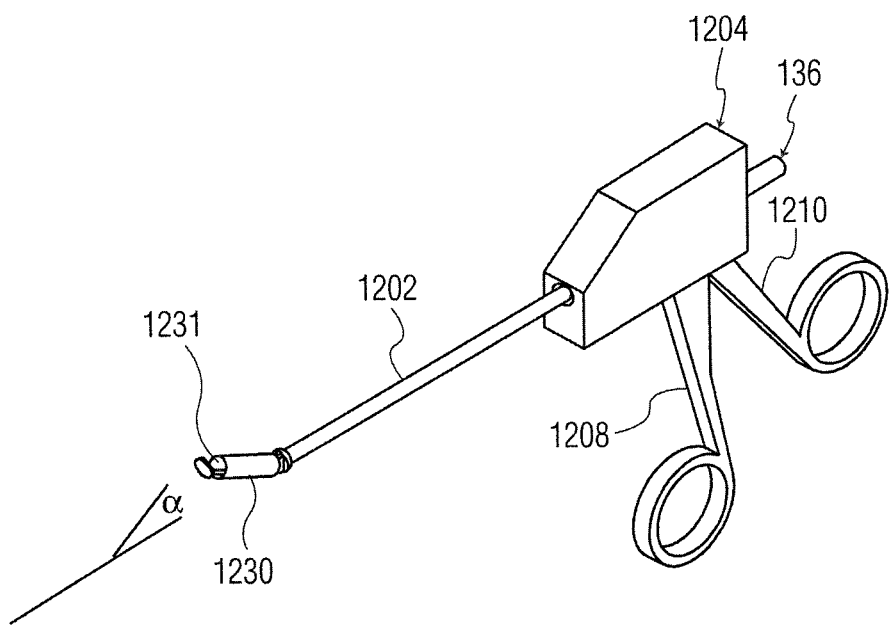
FIG. 12B is an isometric view of the endoscope shown in FIG. 12A.

An isometric view of the endoscope shown in FIG. 12A is shown in FIG. 12B. A lens 1231 is shown mounted to the image acquisition device 1230.

Figure 12C:
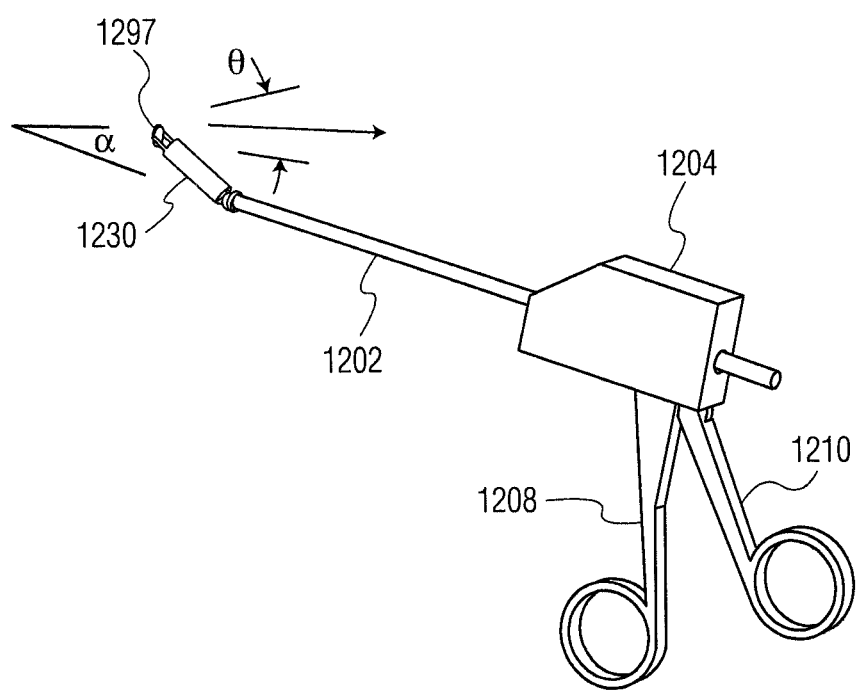
FIG. 12C is another isometric view of the endoscope shown in FIG. 12A.

Another isometric view of the endoscope shown in FIG. 12A is shown in FIG. 12C.

Figure 12D:
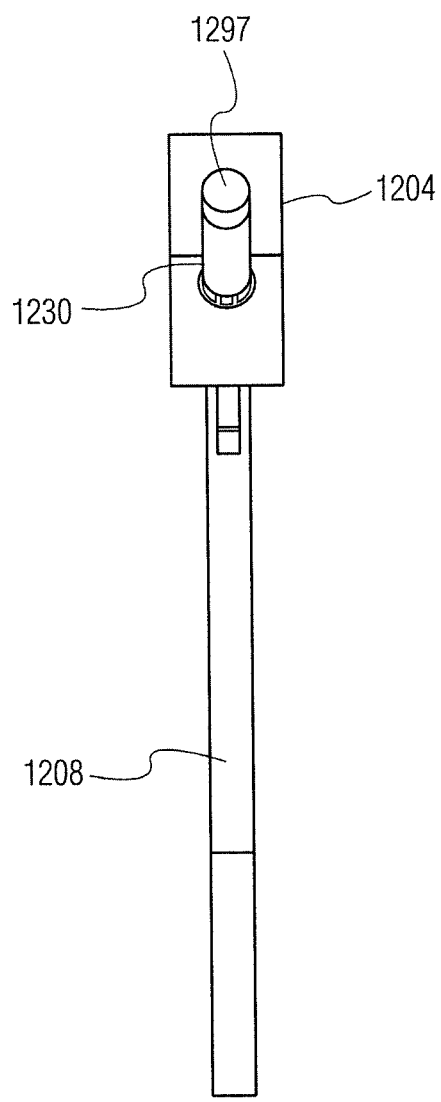
FIG. 12D is a front view of the endoscope shown in FIG. 12A.

A front view of the endoscope shown in FIG. 12A is shown in FIG. 12D.

Figure 12E:
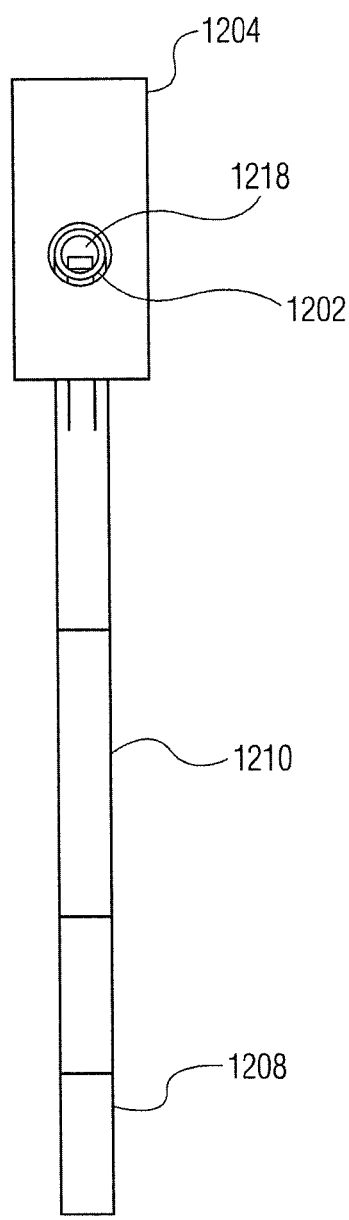
FIG. 12E is a back view of the endoscope shown in FIG. 12A.

A rear view of the endoscope shown in FIG. 12A is shown in FIG. 12E. The shaft 1218 is shown in the elongated section 1202. The shaft may be coupled to the second scissor-type handle 1210 using any suitable method. A biasing member may return the second scissor-type handle 1210 to a default position. In other embodiments, it is envisioned that the second scissor-type handle 1210 may be coupled in a fixed position relative to the handle portion 1204 while the first scissor-type handle 1208 may be coupled in a movable position relative to the handle portion 1204.

Figure 12F:
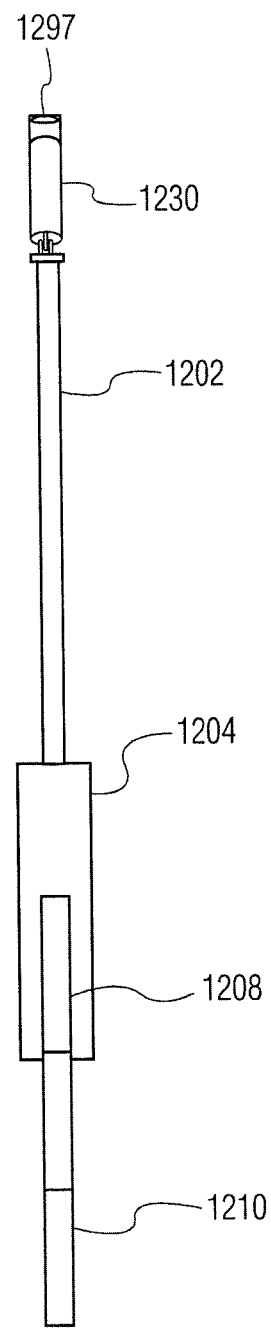
FIG. 12F is a bottom view of the endoscope shown in FIG. 12A.

A bottom view of the endoscope shown in FIG. 12A is shown in FIG. 12F. The handle portion 1204 may be removable from the elongated section 1202.

A perspective view of an endoscope according to another embodiment of the present system is shown in FIG. 13A and FIG. 13B is a detailed view of a distal end of the endoscope shown in FIG. 13A.

With reference to FIG. 13A and FIG. 13B, an endoscope 1300 according to the present embodiment may include one or more of an elongated section (or barrel section) 1302, a handle portion 1304, and a distal portion 1306.

The handle portion 1304 may include first and second grip portions 1308 and 1310, respectively, each of which may be suitable for grasping by a user and which may include one or more grip openings 1313 suitable for receiving a user's fingers. The grip portions 1308 and 1310 may be hingedly or slidably located relative to each other.

The elongated section 1302 may be removably attached to the handle portion 1304 and may include an opening such as a channel which may include a shaft 1318. The shaft 1318 may be coupled to the second grip portion 1310 using any suitable mechanism. For example a hinge, friction, latch, cam, or other mechanism may be used to couple the shaft 1318 to the second grip portion 1310.

The distal section 1306 may include one or more of a first element 1320, a second element 1360, and an end part 1305.

The end part 1305 may include a base portion 1322. Further, the end part 1305 may include one or more image acquisition devices 1330. The one or more image acquisition devices 1330 may capture images one or more viewing directions as illustrated by arrow 1309. The image acquisition device 1330 may include one or more of a focal plane array, a CCD, a memory, a controller, a power supply, and a transmitter/receiver Tx/Rx. The image acquisition device may also include more than one image capture devices such as two or more focal plane arrays 1337, which can capture, for example, stereoscopic (e.g., 3D) images. As image acquisition devices are described elsewhere in this document, and for the sake of clarity, a further description thereof will not be given. However, in other embodiments, it is envisioned that one or more of the memory, the controller, the power supply, and the transmitter/receiver Tx/Rx may be mounted elsewhere. For example, in one embodiment, the Tx/Rx may be located in a handle portion. The end part 1305 may include one or more optically reflective surfaces, or parts thereof, so as to reflect images. For example surface 1331 may include an optically reflective part which can reflect images in those portions which do not optically cover a focal plane array. It is also envisioned that in another embodiment, a further image acquisition device 1330-1 may be mounted within the end part 1305 such that images in another viewing direction as illustrated by arrow 1395 may be captured. Thus, depending upon available space, a user may obtain images in a desired direction. Further, a switchable optical element (e.g., a mirror, prism, etc.) may be included so as to direct images from a desired view to the CCD. Thus, a single CCD array may be used to capture images from two or more views. However, in other it is also envisioned that each image acquisition device may capture images independently of the other.

The first element 1320 may be coupled to the shaft 1318 at a first end and may be coupled to the base portion 1322 at a second end. The second extension element 1360 may be coupled to the elongated section 1302 at a first end and may be coupled to the base portion 1322 and a second end. Any suitable method may be used to couple the first and second extension elements 1320 and 1360, respectively, to the base portion 1322. For example, hinged joints 1324 and 1326 may be used. The hinged joints 1324 and 1326 may include, for example, pins, rivets, threaded members, flexible elements, etc.

A detailed view of a distal end of the endoscope shown in FIG. 13A is shown in FIG. 13C. In operation, displacement of the second grip portion 1310 towards the first grip portion 1308 may cause a displacement of the shaft 1318 within the elongated section 1302. The displacement of the shaft 1318 may cause the first extension element 1320, which is coupled to the shaft 1318, to move a corresponding amount as illustrated by arrow 1391. However, as the second extension element 1360, which is coupled to the handle portion 1304 via the elongated shaft 1302, remains stationary or moves only slightly, the movement of the first extension element 1320 may then cause the base 1322 to rotate about one or more of joints 1324 and 1326. Accordingly, the base 1322 may rotate as illustrated by arrow 1393. Thus, an image viewing direction as illustrated by arrow 1397 may change according to deflection of one of the first or second grip portions 1308 and 1310, respectively, relative to the other of the grip portions 1308 and 1310, respectively.

A partially exploded view of a distal end of the endoscope shown in FIG. 13A is shown in FIG. 13D. The endoscope 1300 may be disassembled for cleaning, servicing, etc. Thus, connection portions for releasably connecting individual components of the endoscope together may be included.

A perspective view of an endoscope according to another embodiment of the present system is shown in FIG. 14A. Further, FIGS. 14B-14C each illustrate a detailed view of a distal end of the endoscope shown in FIG. 14A; FIG. 14D is a partially exploded view of a distal end of the endoscope shown in FIG. 14A; and FIG. 14E is a detailed partial cutaway view of an end portion of the endoscope shown in FIG. 14A.

With reference to FIGS. 14A-14E, an endoscope 1400 according to the present embodiment may include one or more of an elongated section (or barrel section) 1402, a handle portion 1404, and a distal portion 1406.

The handle portion 1404 may include first and second grip portions 1408 and 1410, respectively, each of which may be suitable for grasping by a user and which may include one or more grip openings 1413 suitable for receiving a user's fingers. The grip portions 1408 and 1410 may be hingedly or slidably located relative to each other.

The elongated section 1402 may be removably attached to the handle portion 1404 and may include an opening such as a channel which may include a shaft 1418. The shaft 1418 may be coupled to the second grip portion 1410 using any suitable mechanism. For example a hinge, friction, latch, cam, or other mechanism may be used to couple the shaft 1418 to the second grip portion 1410.

The distal section 1406 may include one or more of a first element 1420, a second element 1460, and an end part 1405.

The end part 1405 may include a base portion 1422. Further, the end part 1405 may include one or more image acquisition devices 1430. The one or more image acquisition devices 1430 may capture images one or more viewing directions as illustrated by arrow 1409. The image acquisition device 1430 may include one or more of a focal plane array, a CCD, a memory, a controller, a power supply, and a transmitter/receiver Tx/Rx. As image acquisition devices are described elsewhere in this document, for the sake of clarity, a further description thereof will not be given. However, in other embodiments, it is envisioned that one or more of the memory, the controller, the power supply, and the transmitter/receiver Tx/Rx may be mounted elsewhere. For example, in one embodiment, the Tx/Rx may be located in a handle portion. The end part 1405 may include one or more optically reflective surfaces, or parts thereof, so as to reflect images. For example surface 1431 may include an optically reflective part which can reflect images in those portions which do not optically cover a focal plane array. It is also envisioned that in another embodiment, a further image acquisition device 1430-1 may be mounted within the end part 1405 such that images in another viewing direction as illustrated by arrow 1495 may be captured. Thus, depending upon available space, a user may obtain images in a desired direction. Further, a switchable optical element (e.g., a mirror, prism, etc.) may be included so as to direct images from a desired view to the CCD. Thus, a single CCD array may be used to capture images from two or more views. However, in other it is also envisioned that each image acquisition device may capture images independently of the other.

The shaft 1418 may include a distal end which may include a first element 1420 and a second element 1460. Each of the first and second elements 1420 and 1460, respectively, may be shaped and/or formed using a material that may provide a biasing force so as to return one or more of the first element 1420 and the second element 1460 to a predetermined position after they are deflected towards each other as illustrated by arrows 1451. However, it is also envisioned that separate biasing member (e.g., a spring) may be used to supply a biasing force to return the first and second elements 1420 and 1460, respectively, to a predetermined position (or range). Each of the first and second elements 1420 and 1460, respectively, may be formed integrally with, or separately from, each other. Each of the of the first and second elements 1420 and 1460, respectively, may be shaped and sized so as to form at least part of a cam area 1433 and 1435 which may engage a corresponding cam area 1437 at an end of the elongated section 1402. Accordingly, when the shaft 1418 is withdrawn into the elongated section 1402 (as illustrated by arrow 1491), engagement of the cam 1437 with the cam areas 1433 and 1435 which may exert a force which deflects the distal ends of the first and second elements 1420 and 1460, respectively, towards each other, as illustrated by arrows 1451. Further, the cams may have any suitable profile. Any suitable method may be used to couple the first and second elements 1420 and 1460, respectively, to the shaft 1418.

With reference to FIG. 14C, deflection of the second grip portion 1410 towards the first grip portion 1408, may displace the shaft 1418 within the elongated section 1402 as illustrated by arrow 1491. This displacement may cause the engagement of the cam 1437 with the cam areas 1433 and 1435 which may exert a force which deflects the distal ends of the first and second elements 1420 and 1460, respectively, towards each other, as illustrated by arrows 1451. The deflection of the distal ends of the first and second elements 1420 and 1460, respectively, towards each other may then cause the base 1422 to rotate about one or more of joints 1424 and 1460. Accordingly, the base 1422 may rotate as illustrated by arrow 1493. Thus, an image viewing direction, as illustrated by arrow 1409, may change according to deflection of one of the first or second grip portions 1408 and 1410, respectively, relative to the other of the grip portions 1408 and 1410, respectively.

With reference to FIG. 14D, the endoscope 1400 may be disassembled for cleaning, servicing, etc. Thus, connection portions for releasably connecting individual components of the endoscope together may be included.

With reference to FIG. 14E, the base portion 1422 is shown slightly rotated and may rotate about 90 degrees (or other amounts) such that the one or more image acquisition devices 1430 may capture images one or more viewing directions as illustrated by arrow 1409. However, it is also envisioned that an image may be reflected off of the surface 1431 and viewed by a user or captured by another endoscope.

A detailed partial cutaway view of an end portion of an alternative embodiment of the endoscope shown in FIGS. 14A-14E is shown in FIG. 14F. The endoscope is essentially similar to the endoscope shown in FIGS. 14A-14F and, for the sake of simplicity, like numerals are used. However, one or more of the joints 1424 and 1426 may include a cam and as fastening device (e.g., a pin, a screw, etc.) in the joint 1426 may act as a follower which engages the cam. For example, a cam may be formed in the shape of an opening 1423 in the base portion 1422, as shown in FIG. 14F. Accordingly, deflection of the distal ends of the first and second elements 1420 and 1422, respectively, towards each other may then cause the base 1422 to rotate (as illustrated by arrow 1493). Thus, an image viewing direction, as illustrated by arrow 1497, may change according to deflection of one of the first or second grip portions 1408 and 1410, respectively, relative to the other of the grip portions 1408 and 1410, respectively. The cam may have any suitable profile which may provide for a given amount of rotation for a given deflection of the first and/or second elements, 1420 and 1422, respectively.

Although, exemplary embodiments shown in one or more of the figures illustrate a fixed first grip portion and a movable second grip portion, it is envisioned that in other embodiments either of these portions may be fixed and/or moveable. Further, one or more of the grip portions may be coupled to the shaft such that deflection of a grip portion in a first direction may cause the shaft to deflect in the same or in an opposite direction. Moreover, linkages may be used to control an amount of deflection of the viewing direction and/or the shaft in relation to a deflection of one of the grip portions.

Further, in other alternative embodiments, the endoscope of the present system may include an encoder for providing information relating to an amount of deflection of the distal portion relative to an absolute point (e.g., the elongated section). This information may be displayed using mechanical means and/or a display such as, for example, a liquid crystal display (LCD). Moreover, an image stabilization system, as is known in the art, may be used to stabilize images (either mechanically and/or electronically) which are received from the endoscopes according to the present system.

With regard to lighting modes, various lighting modes that may be employed by the present system to provide desired lighting characteristics. For example, in one lighting mode, lighting sufficient for providing a view to a surgeon may be provided. However, other lighting modes may correspond with lighting modes which may output one or more wavelengths or spectrums which may be better able to, for example, detect abnormalities. Accordingly, in one embodiment of the present system, a lighting mode may output one or more wavelengths or spectrums which may be better able to detect the present of, for example, cancerous cells, as is known in the art. According to yet another embodiment of the present system, another lighting mode may output light in accordance with a Narrow Band Imaging™ (NBI) routine, which is known in the art and can provide images with enhanced clarity. According to a further object of the present system, one or more image processing applications may be provided to process image information of a surgical field and determined the presence of certain abnormalities such as, for example, cancerous cells.

The present system may be used in various surgical routines which may include, example, Natural Orifice Translumenal Endoscopic Surgery (NOTES) and/or single incision surgery which may be referred to as Laparo-Endoscopic Single Site (LESS) surgery.

The present system may also be retrofitted upon conventional endoscopes and/or may incorporate the use of an off-the-shelf capsule-type imaging system.

Further, to provide images with depth perception such as, for example, stereoscopic and/or 3D images, where each image acquisition device (or the like) according to the preset system may include stereoscopic image capture devices and/or two or more image capturing devices for capturing stereoscopic and/or 3D images, such as disclosed by, for example, U.S. Patent Application No. 2007/0249932 A1, entitled Remote Manipulator with Eyeballs, the contents of which are incorporated herein by reference. Thus, two or more cameras, optical elements such as, mirrors, prisms, imaging arrays (e.g., CCD and/or CMOS arrays), etc. may be included to capture images. Further, the present system may process two or three dimensional images and/or display these images using a suitable display, such as, for example, a two or three dimensional display.

The endoscope of the present system is ideal for performing minimally invasive endoscopic procedures such as, for example, neurosurgery, brain surgery, abdominal surgery, etc. In addition, the present systems, devices and methods may be used in any application requiring entry through (small) openings while minimally disturbing the surrounding environment.

Thus, according to the present systems and devices, an accurate, convenient, low-cost, upgradeable, reliable, and standardized endoscopic imaging system is provided.

Although the present system has been described with reference to an endoscopic imaging system, it is also envisioned that the present system can be extended to other imaging systems such as a laparoscopic endoscope. Accordingly, the present system may be used to capture and/or record image information related to endoscopic imaging applications. Further, the present system may also include a program which may be used with conventional imaging systems so that they may provide features and advantages of the present system.

Certain additional advantages and features of this invention may be apparent to those skilled in the art upon studying the disclosure, or may be experienced by persons employing the novel system and method of the present invention, chief of which is that a more reliable image acquisition system and method of operation thereof is provided. Another advantage of the present systems and devices is that conventional medical image systems can be easily upgraded to incorporate the features and advantages of the present systems and devices.

Of course, it is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

In interpreting the appended claims, it should be understood that:

a) the word "comprising" does not exclude the presence of elements or acts other than those listed in a given claim;

b) the word "a" or "an" preceding an element does not exclude the presence of a plurality of such elements;

c) any reference signs in the claims do not limit their scope;

d) several "means" may be represented by the same item or by the same hardware- or software-implemented structure or function;

e) any of the disclosed elements may be comprised of hardware portions (e.g., including discrete and integrated electronic circuitry), software portions (e.g., computer programs), and any combination thereof;

f) hardware portions may be comprised of one or both of analog and digital portions;

g) any of the disclosed devices or portions thereof may be combined or separated into further portions unless specifically stated otherwise;

h) no specific sequence of acts or steps is intended to be required unless specifically indicated; and i) the term "plurality of" an element includes two or more of the claimed element, and does not imply any particular range or number of elements; that is, a plurality of elements may be as few as two elements, and may include an immeasurable number of elements.

What is claimed is:

1. An endoscopic imaging system comprising:
an endoscope for providing one view of a first view and a second view;
a further endoscope for providing another view of the first view and the second view and
a display,
the endoscope comprising:
a rigid section having opposed first and second ends and an opening situated between the first and second ends, the rigid section defining a longitudinal axis,
at least one handle suitable for grasping by a user and located adjacent to a first end of the rigid section;
a base part having an image capturing device situated at the second end of the rigid section and configured to provide the first view when pointed in a first direction, wherein the base part is coupled to the at least one handle such that displacement of the at least one handle causes a change in a viewing direction of the image capturing device including providing the second view which is different from the first view, wherein the base part is pivotably coupled to the rigid section;
a rigid shaft located in the opening and operatively coupling the at least one handle and the base part, the rigid shaft having an extension portion which is pivotably coupled to the base part at a first pivot portion of the base part, wherein the extension portion is extendable and retractable in response to the displacement; and
a fixing member having an adjustable position relative to the rigid section, the fixing member being rigidly coupled to the rigid section and pivotably coupled to the base part at a second pivot portion of the base part,
wherein the display is configured to display the one view provided from the endoscope with a first identification including a first color and display the another view provided from the further endoscope as a picture-in-picture displayed on a portion of the display with a second identification including a second color which is different from the first color.

2. The endoscopic imaging system of claim 1, further comprising a transmitter which transmits images captured by the image capturing device.

3. The endoscopic imaging system of claim 2, further comprising a receiver which receives the images captured by the image capturing device.

4. The endoscopic imaging system of claim 3, further comprising one or more controllers which receive the images from the receiver and display the images captured by the image capturing device on the display, the one or more controllers being further configured to control a magnifier to provide a desired amount of magnification of the images captured by the image capturing device.

5. The endoscopic imaging system of claim 1, wherein the base part further comprises a reflective optical element configured to reflect images from portions of an object of interest which are not in a field of view of the image capturing device.

6. The endoscopic imaging system of claim 5, wherein the reflective optical element is configured to reflect images from portions of the object of interest located behind the image capturing device in a rear direction for providing the second view when the image capturing device is pointed in the first direction which is opposite the rear direction.

7. The endoscopic imaging system of claim 1, wherein the image capturing device includes a single plane array for capturing images from two viewing directions for providing stereoscopic images when pointed in the first direction.

8. The endoscopic imaging system of claim 1, wherein the image capturing device is configured to provide a rear view in response to a 90° rotation of the base part.

9. The endoscopic imaging system of claim 1, wherein the base part is configured to cooperate with the rigid shaft and the fixing member to provide a rear view in response to a 90° rotation of the base part.

10. The endoscopic imaging system of claim 1, wherein the viewing direction of the image capturing device is perpendicular to the longitudinal axis when the image capturing device is aligned with the longitudinal axis.

11. The endoscopic imaging system of claim 1, wherein the viewing direction of the image capturing device is perpendicular to the longitudinal axis when the base part is aligned with the longitudinal axis so that rotation of the base part by 90° provides a rear view.

12. The endoscopic imaging system of claim 1, wherein the image capturing device is located on a first side of the base part for providing the first view in the first direction when the base is aligned with the longitudinal axis, and wherein the base part further includes a further image capturing device located on a second side of the base part for providing the second view in a second direction when the base is aligned with the longitudinal axis, the second direction being different from the first direction.

13. The endoscopic imaging system of claim 12, wherein the second direction is perpendicular to the first direction.

14. The endoscopic imaging system of claim 1, wherein the display is configured to display the first view and the second view in different portions of the display.

15. The endoscopic imaging system of claim 1, wherein the first pivot portion of the base part has an oblong opening.

16. The endoscopic imaging system of claim 1, wherein the first pivot portion and the second pivot portion of the base part are located at diagonal corners of the base.

17. The endoscopic imaging system of claim 1, further comprising:
   a further base part being pivotably connected to the rigid shaft and the fixing member at two pivot portions;
   a first arm connecting the base part to the image capturing device; and
   a second arm connecting the further base part to the image capturing device,
   wherein the image capturing device is raised above the longitudinal axis in response to adjusting the adjustable position of the fixing member.

18. The endoscopic imaging system of claim 1, wherein the display is further configured to display an orientation of the image capturing device superimposed over the image captured by the image capturing device.

* * * * *